(12) United States Patent
Atkin

(10) Patent No.: US 10,783,988 B1
(45) Date of Patent: Sep. 22, 2020

(54) SYSTEM, APPARATUS AND METHOD FOR THE WIRELESS MONITORING OF MEDICAL TEST DATA

(71) Applicant: Benjamin Atkin, Miami, FL (US)

(72) Inventor: Benjamin Atkin, Miami, FL (US)

(73) Assignee: SMART METER CORPORATION, New City, NY (US)

( * ) Notice: Subject to any disclaimer, the term of this patent is extended or adjusted under 35 U.S.C. 154(b) by 0 days.

(21) Appl. No.: 16/593,796

(22) Filed: Oct. 4, 2019

Related U.S. Application Data

(63) Continuation of application No. 16/389,373, filed on Apr. 19, 2019, now abandoned.

(51) Int. Cl.
*G01N 1/00* (2006.01)
*G16H 10/40* (2018.01)
*G16H 40/67* (2018.01)

(52) U.S. Cl.
CPC ............. *G16H 10/40* (2018.01); *G16H 40/67* (2018.01)

(58) Field of Classification Search
CPC ........................................ G01N 1/00
See application file for complete search history.

(56) References Cited

U.S. PATENT DOCUMENTS

| | | | |
|---|---|---|---|
| 4,697,380 A | 10/1987 | Fenske | |
| 5,109,625 A | 5/1992 | Skrede | |
| 5,394,639 A | 3/1995 | Tentler | |
| 8,372,351 B2 | 2/2013 | Ow-Wing | |
| 8,875,436 B1 | 11/2014 | Bell | |
| 8,920,725 B2 | 12/2014 | Withrow, III et al. | |
| 8,965,333 B1 | 2/2015 | Shreiber et al. | |
| 10,039,496 B2 * | 8/2018 | Yarger | G06F 19/00 |
| 10,311,208 B2 | 6/2019 | Atkin | |
| 2002/0020104 A1 | 2/2002 | Kolar et al. | |
| 2005/0038680 A1 | 2/2005 | McMahon | |
| 2005/0086851 A1 | 4/2005 | Carden et al. | |
| 2008/0269673 A1 | 10/2008 | Butoi et al. | |
| 2010/0222648 A1 | 9/2010 | Tan | |
| 2010/0228111 A1 | 9/2010 | Friman et al. | |
| 2010/0240979 A1 | 9/2010 | Atkin | |
| 2010/0294660 A1 | 11/2010 | Wang et al. | |

(Continued)

FOREIGN PATENT DOCUMENTS

| | | |
|---|---|---|
| CN | 202083667 U | 12/2011 |
| CN | 102835960 A | 12/2012 |

(Continued)

OTHER PUBLICATIONS

Patents Act 1977: Search Report Under Section 17(5), dated Jan. 28, 2020 for corresponding Application No. GB1910949.5, consisting of 4 pages.

(Continued)

*Primary Examiner* — Jyoti Nagpaul
(74) *Attorney, Agent, or Firm* — David Postolski, Esq.

(57) ABSTRACT

An apparatus for obtaining and transmitting medical test data, comprising a housing containing a processor, memory, and a power source; a display; a wireless transceiver configured to send data of the medical test to a remote location to be recorded in a central database, using at least one of a plurality of wireless communication services; an A1c detector, wherein the medical test is the detection of an A1c value by the A1c detector.

15 Claims, 12 Drawing Sheets

(56) References Cited

U.S. PATENT DOCUMENTS

| | | |
|---|---|---|
| 2011/0081888 A1 | 4/2011 | Waniss |
| 2011/0193704 A1 | 8/2011 | Harper et al. |
| 2013/0112557 A1 | 5/2013 | Javitt et al. |
| 2013/0116526 A1 | 5/2013 | Javitt et al. |
| 2013/0229288 A1 | 9/2013 | Alexander et al. |
| 2014/0046600 A1 | 2/2014 | Avner |
| 2016/0212983 A1 | 7/2016 | Boudreau |
| 2019/0244690 A1 | 8/2019 | Atkin |

FOREIGN PATENT DOCUMENTS

| | | |
|---|---|---|
| CN | 103330567 A | 10/2013 |
| CN | 103472010 A | 12/2013 |
| CN | 103698528 A | 4/2014 |
| CN | 203506709 U | 4/2014 |
| CN | 204116356 U | 1/2015 |
| WO | 2012066278 A1 | 5/2012 |
| WO | 2012126800 A1 | 9/2012 |
| WO | 2015187801 A1 | 12/2015 |

OTHER PUBLICATIONS

Patents Act 1977: Examination Report Under Section 18(3), dated Jan. 27, 2020 for corresponding Application No. GB1620995.9, consisting of 2 pages.

Canadian Patent Search Report, dated Dec. 27, 2017, for corresponding PCT Application No. PCT/US2015/033938, International Filing Date Jun. 3, 2015, consisting of 4 pages.

Musa Unmehopa, "Management and Provisioning of M2M Devices and Applications," OMA Open Mobile Alliance, Retrievable at: http://cn.openmobilealliance.org/wp-content/uploads/2012/11/management-and-provisioning-of-m2m-devices-and-applications.pdf (Accessed Apr. 9, 2018), 22 Pages.

Bradley De Souza, "USSD—A Cheap Alternative to Machine Driven SMS," Retrievable at: http://www.xtanz.com/?p=73 (Accessed Apr. 9, 2018), 2 Pages.

EPO European Patent Search Report, dated Jan. 9, 2018, for corresponding PCT Application No. PCT/US2015/033938, International Filing Date Jun. 3, 2015, consisting of 13 pages.

International Preliminary Report on Patentability, dated Dec. 6, 2016, for corresponding PCT Application No. PCT/US2015/033938, International Filing Date Jun. 3, 2015, consisting of 5 pages.

Written Opinion of the International Searching Authority, dated Nov. 5, 2015, for corresponding PCT Application No. PCT/US2015/033938, International Filing Date Jun. 3, 2015, consisting of 4 pages.

International Search Report, dated Jun. 3, 2015, for corresponding PCT Application No. PCT/US2015/033938, International Filing Date Jun. 3, 2015, consisting of 2 pages.

* cited by examiner

Your Time Zone
(GMT -5:00) Eastern Time (US & Canada), Bogo ▽

Date Range
Custom Date Ra ▽

From:
02/02/2015

To:
05/20/2015

Update Time Zone

Set Default Date Range

Time Range:
From:
12:00 AM

To:
11:59 PM

Patient
All Patients ▽

Device
2313426-SGM 1 ▽

Manage Patients

RESET    FILTER

FIG. 1

Logbook

| Date | Time | Blood Glucose Reading | Before Meal | After Meal | Other |
|---|---|---|---|---|---|
| 02/09/2015 | 6:50 PM | 212 | | | |
| 02/08/2015 | 7:37 PM | 318 | ● | | |
| | 6:58 PM | 316 | ● | | |
| | 11:43 AM | 187 | ● | | |
| | 9:10 AM | 99 | ● | | |
| 02/07/2015 | 8:06 PM | 135 | ● | | |
| | 6:04 PM | 176 | ● | | |
| | 3:55 PM | 190 | | ● | |
| | 1:43 PM | 229 | ● | | |
| | 10:56 AM | 121 | ● | | |
| | 8:03 AM | 162 | ● | | |
| 02/06/2015 | 10:59 PM | 272 | ● | | |
| | 10:08 PM | 227 | ● | | |
| | 9:50 PM | 350 | ● | | |
| | 2:58 PM | 188 | ● | | |
| | 2:49 PM | 201 | ● | | |
| | 9:07 AM | 137 | ● | | |
| 02/05/2015 | 9:37 PM | 171 | ● | | |
| 02/04/2015 | 7:32 PM | 120 | ● | | | print

FIG. 3

Insurance Company

Diabetes: Type 2

Year Diagnosed: 2006

Caring Physician

FIG. 4

Data Recipients

| Name | Email | Emailed Reports |
|------|-------|-----------------|
|      |       | Instant ▾       |

| Device | Patient | Date/Time Format | Healthcare Provider |
|--------|---------|------------------|---------------------|
| All Devices ▾ | All Patients ▾ | MM/DD/YYYY: AM/PM ▾ | No ▾ |

[ADD]

Emailed Reports | Mobile Messaging

FIG. 5

Alerts

Profile
Device Registration
Data Recipients
Alerts
Logout

Add

Name

Email

Range Limits:

Frequency:

Warning Low    Warning High    Emergency Low    Emergency High

☐ Enter # of times Expected per day
☐ Send Alert if under this amount

Phone

Please choose c ⌄

☐ Email
☐ SMS

☐ Email
☐ SMS

ADD

Device
Please choos ⌄

Patient
Please choos ⌄

Date/Time Format
MM/DD/YYYY: AM ⌄

Current Alert Recipients

FIG. 6

Company Name

Name ▾

Readings
Profile
Device Registration
Data Recipients
Alerts
Logout

Device Registration

Current Devices

| Your Name | Device ID | IMEI | |
|---|---|---|---|
| SGM 1 | 2313426 | 359421032313426 | Update |
| | | | Delete |

Activate New Device

| Create A Device Name | Device ID | Confirm Device ID | IMEI | |
|---|---|---|---|---|
| SGM 2 | | | | Add Device |

FIG. 7

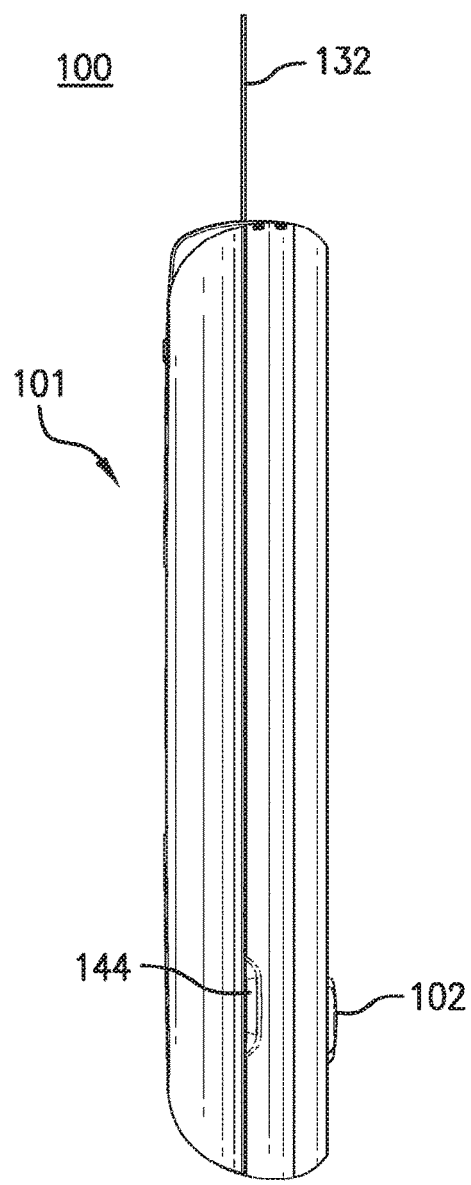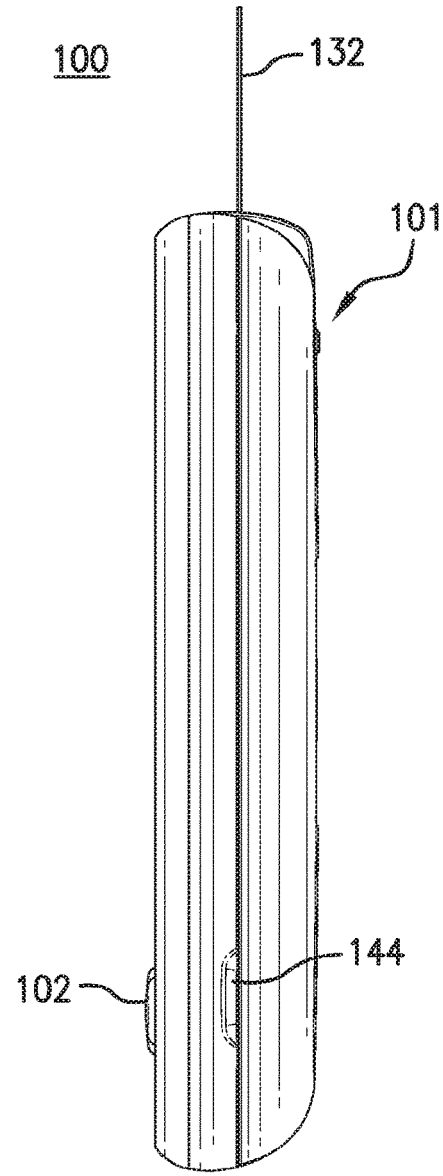
FIG. 11
FIG. 12

SYSTEM, APPARATUS AND METHOD FOR THE WIRELESS MONITORING OF MEDICAL TEST DATA

CLAIM OF PRIORITY

This application is a CIP of U.S. patent application Ser. No. 16/389,301, filed Apr. 19, 2019; which is a Division of patent application Ser. No. 14/729,310 filed Jun. 3, 2015, now U.S. Pat. No. 10,311,208 issued Jun. 4, 2019; which claims priority from Provisional Patent Application No. 62/006,978 filed on Jun. 3, 2014 and U.S. Provisional Patent Application No. 62/169,875 filed Jun. 2, 2015, the contents of all of which are hereby incorporated by reference as if fully set forth herein.

FIELD OF THE EMBODIMENTS

The embodiments relate to a system, method and apparatus to be used for various types of medical tests in which test results are automatically transmitted to a remote server and stored. In particular, the apparatus enables cellular or other wireless transmission, storage, monitoring, notifications, and the like to keep individual users and third parties apprised of at least one medical test result.

BACKGROUND

It is estimated that diabetes care costs in excess of $218 billion in the U.S. The $218 billion amounts to about 10 percent of all U.S. health care spending by government and the public, about $2.1 trillion in 2006, and nearly half the $448.5 billion cost of heart disease and stroke. Diabetes mellitus, or diabetes as it is commonly known, includes several different metabolic disorders that result in high concentrations of glucose, a sugar, in the blood. It is currently estimated that diabetes care costs in excess of $240 billion in the U.S every year alone. This $240 billion figure amounts to about 10% of all U.S. health care spending.

In order to help treat the diabetes, a person may be prescribed diet changes, medications, insulin. However, a person must still be cognizant of their blood glucose levels to prevent a drop or spike in blood glucose levels which may lead to various ailments including, in severe cases, coma and death. Thus, diabetic persons should monitor their blood glucose levels with the aid of a glucose meter. Optimal measurement involves a patient measuring and recording their blood glucose levels over a period of time and in relation to certain events (i.e. eating and exercise). By understanding what effects food and exercise have on their blood glucose levels, appropriate lifestyle shifts can be made.

However, current blood glucose meters have several drawbacks. For example, blood glucose meters often lack the ability to communicate with another remote location such as a doctor's office. Thus, in order to a doctor to be kept apprised of a diabetic's situation, they have to assume the diabetic patient is testing themselves regularly and being truthful in their test results.

Thus, there is a need for a blood glucose meter that can automatically send test results to a remote location for instant analysis. This allows, for example, an alert or notification to be generated and sent to family members if a person's blood glucose level is such that it may signify that are in or about to be in danger of becoming hypoglycemic or hyperglycemic. The described embodiments meet and exceed these objectives.

Examples of related art are described below: U.S. Patent Publication No. 20100240979 discloses a system and method for transmitting blood glucose level information related to time and date from a user via a glucometer using the Global System for Mobile Communications (hereinafter GSM) modem, an antenna, meter interface, and microprocessor. U.S. Pat. No. 8,372,351 discloses a glucose monitoring with wireless communication and pairing capabilities via Bluetooth. U.S. Patent Publication No. 20130112557 discloses a glucose monitor with a temperature sensor to mitigate the effects of heat on a blood sample. U.S. Patent No. 20100228111 teaches a blood glucose measuring module and a wireless communication module which are physically-separate units electrically connected in order to allow for an exchange of electrical signals. U.S. Patent Publication No. 20080269673 teaches a cellular enable medical monitoring and infusion system paired with an infusion pump. U.S. Patent Publication No. 20050038680 teaches a cellular enabled medical infusion device for inputting medical data via a cellular network. U.S. Pat. No. 8,965,333 teaches a remote monitoring system and method utilizing wireless network of a plurality of contiguous decoded data packages. U.S. Patent Application 2013/0116526 pertains to a patient monitoring network pertaining to blood glucose and other analyte measurements includes wireless blood glucose or other analyte measuring devices and a networked computer or server. Each monitoring device is associated with a patient and is configured to measure the glucose level or other analyte from a given blood sample via inserted test strips, transmit the measurements to the networked computer, and display received messages. The messages may relate to the current or past measurements, or may include an alert prompting the user of the monitoring device to order more supplies, such as test strips. The measurements received by the networked computer may be stored in a record of a database, which may be accessed by a remote computer. The remote computer may also access a script editor to edit certain scripts which produce certain messages sent to the monitoring device.

International Patent Publication No. WO2012066278A1 teaches a server-side initiated communication unrelated to glucose monitoring. International Patent Publication No. WO2012126800A1 teaches calculating a dose of insulin based on information being transmitted from a meter the focus of the patent is on the dosing of insulin and discusses getting data via wireless communication. Chinese Patent No. CN2041 16356U simply discloses a SIM Card based Glucose meter and pertains to a SIM card based medical meter. The device includes a glucose meter, SIM cards, and test strips. The SIM card contains five modules, namely communications (CPU), working memory (RAM), program memory (FLASH ROM), EEPROM data memory and serial communication unit with the CPU. The SIM card is inserted into the meter installed SIM card slot, the test strips into the blood glucose meter test strips slot. The Sim card is read and stored in the EEPROM module. The blood glucose meter reads the test strip in contact with the test sample, the meter reads the data and stores it in the SIM card. Chinese Patent No. CN102835960 entitled "Portable intelligent glucometer supporting measured data to be real timely sent through mobile short messages" only discloses short message service (SMS) via GSM. Chinese Patent No. CN103472010A teaches a diabetes detection device using a user's blood and urine. Chinese Patent No. CN103330567A discloses a GPRS glucometer with identification function but focuses on RFID. Various devices are known in the art. However, their structure and means of operation are substantially different from disclosed embodiments. Accordingly, there is a need for a device to assist the diabetic community transmit and receive blood glucose readings in an efficient and most reliable manner. At least one embodiment is presented in the drawings below and will be described in more detail herein.
Medical Record/Medical Device Integration Having identified the problem/opportunity within this $218 billion market, we can now establish the necessity for a glucose meter that can share data and integrate with electronic medical records with extreme reliability. The system is designed with triple redundancy and extreme reliability. Every Glucose reading is life and death to a diabetic patient. Accordingly, health care and service providers need to be notified upon a moment's notice. Known in the art are glucometers which read blood glucose sample and require an additional step for the blood glucose result to be transmitted to a diabetic patient's primary care physician. The present system eliminates this additional step and allows for a blood glucose reading to automatically and instantaneously delivered to a plurality of designated individuals at a desired frequency and through multiple communication methods, each of which are built into the device and supporting software systems. The system supports 3 communication methods SMS, GPRS and USSD as explained below.

The system and device transmits, receives and delivers blood glucose readings and messages through Unstructured Supplementary Service Data (hereinafter USSD), a protocol according to the GSM standard. [The GSM was developed by the European Telecommunications Standards Institute (ETSI) to describe protocols for digital cellular networks used by mobile phones to communicate with a service provider's computers.] USSD is used for wireless application protocol browsing, prepaid callback service, mobile-money services, location-based content services, menu-based information services, and as part of configuring a phone on a network. USSD messages are up to 182 alphanumeric characters in length. USSD messages create a real-time connection and remains open, allowing a two-way exchange of a sequence of data.

The system and device transmits, receives and delivers blood glucose readings and messages through Greedy Perimeter Stateless Routing (GPSR). GPSR, is an efficient routing protocol for mobile, wireless networks. GPSR is a geo routing method wherein data packages are not sent to a special receiver but to network coordinates according to a greedy algorithm (i.e. a network coordinate that is local, and the optimally closer to the destination). Data packages are relayed to a node that's geographically closest to the coordinates.

The system and device transmits, receives and delivers blood glucose readings and messages through Short Message Service (hereinafter SMS). SMS is a text messaging service component of phone, Web, or mobile communication systems. It uses standardized communications protocols to allow fixed line or mobile phone devices to exchange short text messages.

The system and device utilizes the ACCU-CHEK Inform II system which offers healthcare professionals the first truly wireless hospital blood glucose device. The system utilizes technology to deliver improved accuracy and enables automatic real-time wireless transfer of patient data between hospital medical staff and the laboratory. The system and device utilizes a mobile approach to diabetes education and support. The system enables a patients profile to be personalized in order to help people with type 2 diabetes take better control of their condition. The software based program, entitled Care2Life focuses on education and adherence to the participant's treatment protocol. It also allows participants to build an electronic record of blood glucose readings, blood pressure, weight and exercise that they can view on-line and share with their providers.

Current attempts, devices, systems and methods known in the art are deficient. Traditionally and unbelievably, most methods, devices and software platforms capture data from their diabetic patients manually, disclosed embodiments can easily be integrated in a meaningful way with electronic medical record (hereinafter EMR) companies. The Smart Glucose Meter is a glucose meter that not only can share data but does so easily, seamlessly and technologically advanced, automatically integrating with electronic medical records.

There are more than two dozen studies that depict results requiring capture of diabetes data to manage this disease. Yet to date, there exist but one device owned by Telcare, Inc. that has developed an automatic method to capture this data. However, the Telcare device does not share data with other Electronic Medical Record platforms or systems. The present system and device is an Open Application interface and data can be pushed and pulled from a variety of electronic medical record software's, programs, and systems.

Various other systems and methods are known in the art as described above. However, their structure and means of operation are substantially different from the present disclosure. The other systems and methods fail to solve all the problems taught by the present disclosure. At least one embodiment is presented in the drawings below and will be described in more detail herein.

SUMMARY

Apparatus for obtaining and transmitting medical test data, comprising a housing containing a processor, memory, and a power source; a display; a wireless transceiver configured to send data of the medical test to a remote location to be recorded in a central database, using at least one of a plurality of wireless communication services; and an A1c detector, wherein the medical test is the detection of an A1c value by the A1c detector.

Embodiments may also include apparatus for transmitting and receiving medical test data is provided comprising memory that stores computer-executable instructions; processor, communicatively coupled to the memory that facilitates execution of the computer-executable instructions; and comprising: a transmission means operatively associated with a device, a receiver adapted and configured to receive data from said transmission means; a central database adapted and configured to compile said data; wherein said data is transformed into an output comprised of an aggregate of medical test data from at least one medical test. The computer implemented method for transmitting and receiving medical test data comprises the steps of transmitting means operatively associated with a device, receiving data from said transmission means; compiling said data into a central database; and transforming said data from the database into an output comprised of an aggregate of medical test data from at least one medical tests.

In embodiments, the device is a glucometer and/or an A1c meter, and the medical test is a blood glucose measurement or A1c measurement or estimate. The transmission means includes a direct connection, wireless transmission, or combinations thereof. The transmission means includes a configuration to encrypt said medical test data. The receiver is adapted and configured to receive encrypted transmissions from said transmission means and to unencrypt said data. The transmission means includes a transmission protocol of at least one of a Greedy Perimeter Stateless Routing (GPSR) routing protocol, short text messages (SMS), Unstructured Supplementary Service Data (USSD), and at least one cellular standard such as at least one of 2G, 3G, 4G, 5G, and CAT-M data service. The receiver is adapted and configured to communicate with the device and said communication includes a signal in which receipt of transmitted data is confirmed. The database compilation of test data is transmitted to and received from at least one of a patient, healthcare provider, insurance/medical benefits provider, and combinations thereof. The database is adapted and configured to provide an actuated transmission when particular medical test thresholds are transmitted. The actuated transmission includes a warning to a patient, healthcare provider, insurance/medical benefits provider, or combinations thereof relating to transmission of data at a threshold level. The threshold level is a medical test result above or below a threshold limit.

Generally, disclosed embodiments provide for an improved medical testing device. In the main context of the application, it is contemplated that such a medical testing device will embody a blood glucose meter. However, any number and type of medical tests may be performed using the same principles and apparatus as described herein.

The apparatus has a wireless transceiver that enables wireless transport of data associated with the medical test, in this case, a blood glucose measurement. This enables the blood glucose measurement to be sent to a remote location such as a server, family member, doctor, or the like or a combination thereof. In some instances, it is sent to a doctor, who can then automatically generate an alert to family members or send proper personnel or other appropriate response in response to a high or low medical test result for that person. In other instances, such an alert or notification is automatically generated and sent out in response to an abnormal result.

In one embodiment there is an apparatus for collecting and transmitting medical test data, the apparatus having an external housing having a power source, processor, and a memory contained therein with the memory being operably coupled to the processor; a display for displaying information associated with at least one medical test; a wireless transceiver configured to send collected medical test data to a remote location; at least one receptacle configured to receive a medical testing apparatus, wherein an analytical tool analyzes the medical testing apparatus to generate a medical test result; a slidable member coupled to the at least one receptacle, wherein sliding of the slidable member causes the medical testing apparatus to be removed from the at least one receptacle; and a power source for powering of the apparatus.

It is an object of disclosed embodiments that the wireless communication automatically initiates and transmits upon completion of a medical test.

It is an object of disclosed embodiments wherein the glucometer has wireless communication that automatically initiates and transmits upon completion of a blood glucose test.

It is an object of disclosed embodiments wherein the medical test data is wirelessly and automatically uploaded to the device.

It is an object of disclosed embodiments wherein a plurality of said medical test data is assigned a unique data profile corresponding to a plurality of users, said unique data profile configurable to include at least one of individuals, medical service providers and professionals and medical insurance providers.

It is an object of disclosed embodiments wherein medical test data is transformed into a plurality messages.

It is an object of disclosed embodiments wherein the plurality of messages are transmitted as real time alerts corresponding to the medical test data of a plurality of users.

It is an object of disclosed embodiments wherein the plurality of messages comprises at least one of short text message (SMS), GPRS Greedy Perimeter Stateless Routing, and voice channels.

It is an object of disclosed embodiments wherein the frequency and method of transmission is configurable and adjustable.

It is an object of disclosed embodiments wherein the plurality of messages comprise an electronic medical record of a user.

It is an object of disclosed embodiments wherein data is transmitted and received from a plurality of electronic medical record platforms and systems.

It is an object of disclosed embodiments wherein the data is transformed and stored on a subscriber identification module, said subscriber identification module being physical or virtual.

It is an object of disclosed embodiments wherein at least one of the plurality of messages is deemed redundant for verification and synchronization of the plurality of messages with said central database.

It is an object of disclosed embodiments wherein the medical test data is transformed into a plurality of languages.

It is an object of disclosed embodiments that the system comprises an advertising module.

BRIEF DESCRIPTION OF THE DRAWINGS

FIG. 1 is an illustrative view of a display box in accordance with the disclosure.

FIG. 3 is an illustrative view showing a logbook where the date and time period of a recorded blood glucose reading is displayed.

FIG. 4 is an illustrative view of a user's profile in accordance with the disclosure.

FIG. 5 is an illustrative view of the Data Recipients screen in accordance with the disclosure.

FIG. 6 is an illustrative view of the Alerts screen in accordance with the disclosure.

FIG. 7 is an illustrative view of the Registration screen in accordance with the disclosure.

FIG. 11 is a left side view of an embodiment in accordance with the disclosure.

FIG. 12 is a right side view of an embodiment in accordance with the disclosure.

DETAILED DESCRIPTION

Figure 2:
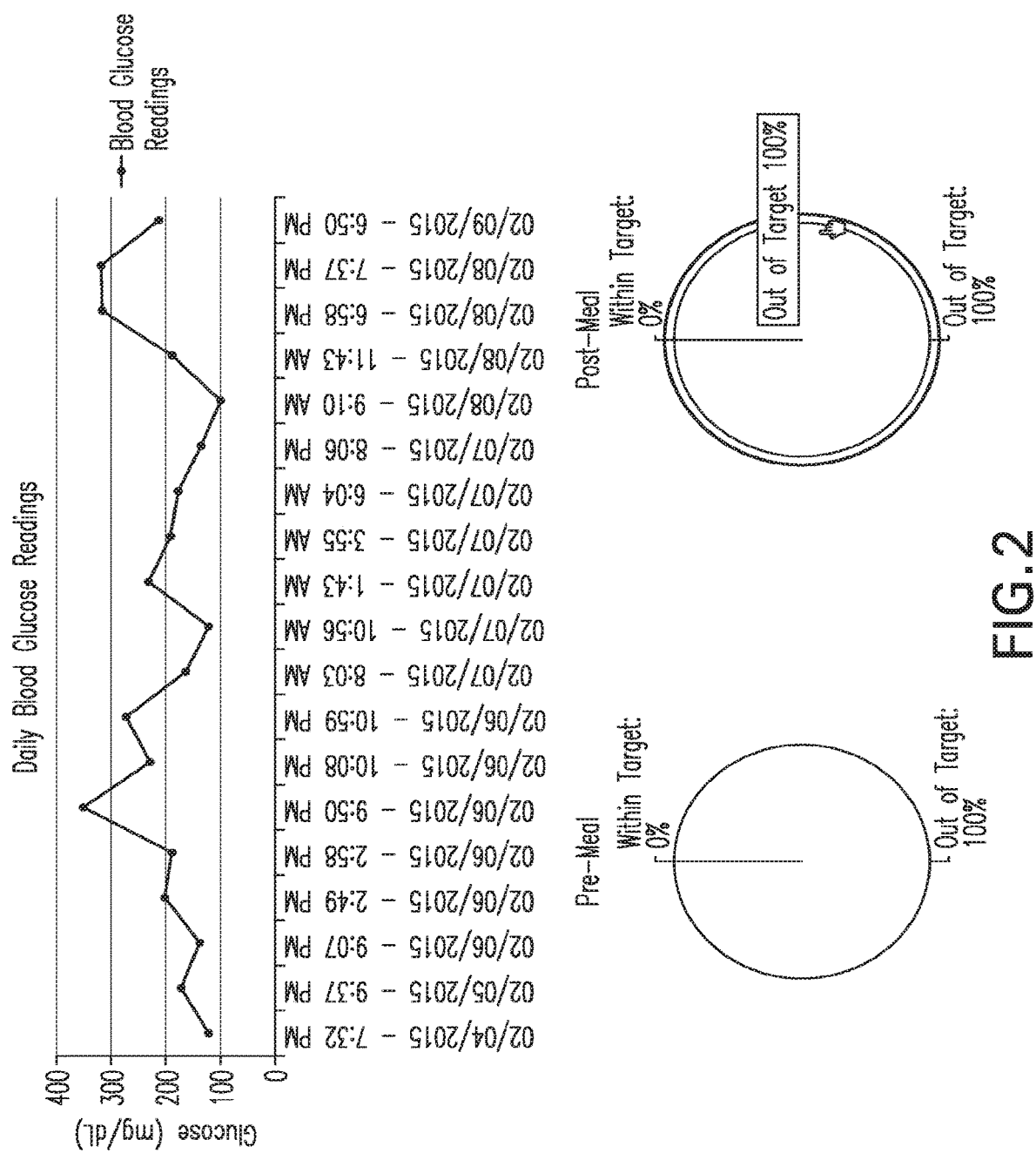
FIG. 2 is an illustrative view of a representative example of daily blood glucose readings in accordance with the disclosure.
Figure 8:
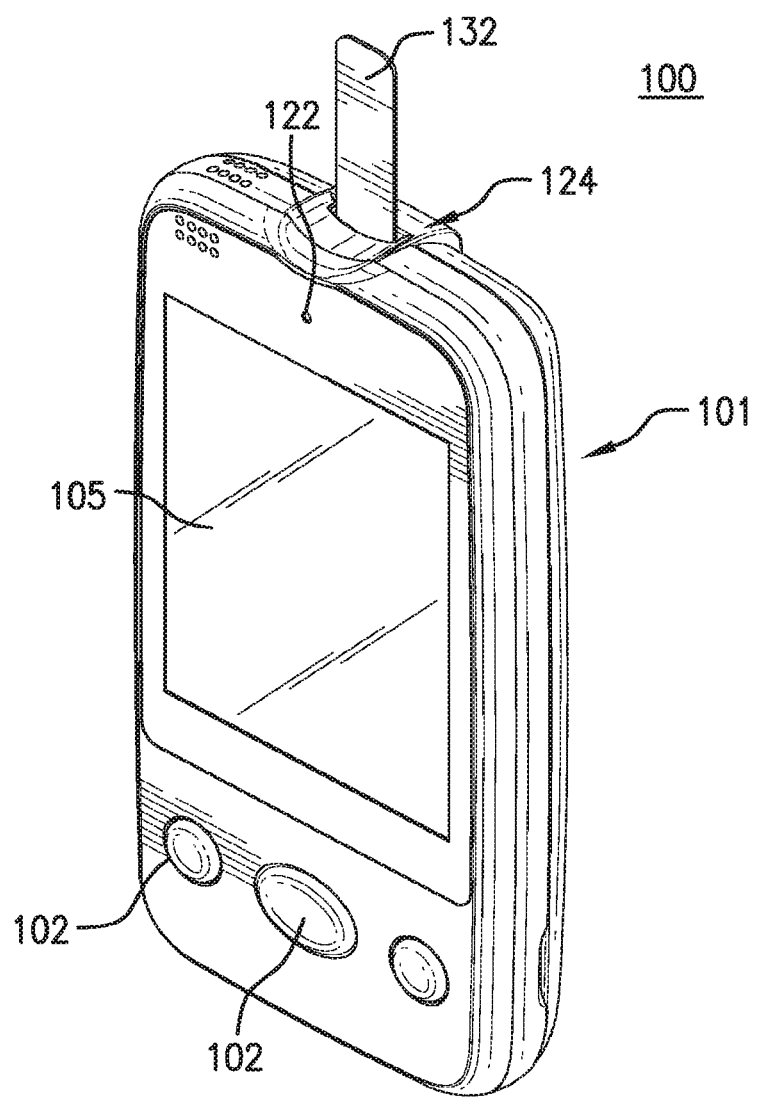
FIG. 8 is a perspective view of an embodiment in accordance with the disclosure.

Illustrative embodiments and aspects will now be described with reference to the drawings. Identical elements in the various figures are identified with the same reference numerals.

The described embodiments are provided by way of explanation, which is not intended to be limited thereto. In fact, those of ordinary skill in the art may appreciate upon reading the present specification and viewing the present drawings that various modifications and variations can be made thereto.

The system, methods and device of the described embodiments utilize a software based system and device which contain the following screens and displays and are meant to be illustrative and representative. FIG. 1 is a perspective view of a display box displaying a user may set the date range and so that medical test data will appear. A user may set the time zone where the user is located or the device may automatically recognize the time zone where the user and device is located. The user may select a time range as well as set these ranges to a default setting. The system and device allows for the storing of multiple users. Thus a user of the device may select what user's records or data they want to view. The device may store up to 35 users or patients. Each user or patient is assigned an identification number such as P1 or P35. In another embodiment, the user may select for other fields to be displayed.

FIG. 2 is an illustrative example of daily blood glucose readings. The above graph shows tracks the blood glucose readings or scores which are recorded over a specified range of dates and times. For example on Feb. 4, 2015 at 7:32 pm the blood glucose score was slightly above 100 Milligrams per Deciliter (mg/dL) while on Feb. 8, 2015 at 6:58p.m. the user's blood glucose score was slightly over 300 mg/dL. In the pie charts below, the average reading is shown as being within the target range of a normal blood glucose level before a meal (pre-meal) and whether the reading was within the target range of a normal blood glucose reading after a meal (post meal). A user may set a range of where they desire their score to be and the pie chart can determine if a user's blood glucose readings are within that desired range. In another embodiment, the graphs may be pie charts, bar graphs or color graphs. The graphs may only display information from a particular day, time period or blood glucose reading. Time may be recorded in hour, minutes and seconds. In another embodiment, the user may select the type of graph they desire and the desired medical test data they want displayed. A user may select the time format and date format of his choosing. Additional data to be recorded include temperature in Fahrenheit or Celsius, FIG. 3 is an illustrative view showing a logbook where the date and time period of a recorded blood glucose reading is displayed. A user's average blood glucose readings (as recorded from a test strip) are displayed in chart formation showing the date, time, blood glucose reading, and whether the reading was before or after a meal. The log book may be printed or emailed to a designated individual. In another embodiment the log book may be in different display forms. In another embodiment a user may select other data to be displayed. In another embodiment the data or portions of the data can be extracted and sent to a designated individual such as a medical service provider. A user's average blood glucose readings are saved in the device for a specified period of time and are further stored in the systems software as well as in the cloud storage unit of each user and health care provider of each The system, device and corresponding software allow a user to create a profile. FIG. 4 is an illustrative view of a user's profile. In addition to a user entering his personal and medical information, a user is able to enter his insurance information, diabetes type, year of diagnosis and treating doctor. In another embodiment a user may enter all physicians who are treating each specified user.

FIG. 5 is an illustrative view of the Data Recipients screen.

The user of the system or device may choose their intended recipient of medical test data and whether the recipient received the data via an email or text, the frequency of those messages, the date and time the message or transmission is to be sent, and whether the recipient is a healthcare professional. A user may display a listing of all emailed reports sent to a particular recipient. The system is able to send messages and data from multiple devices of multiple users to multiple recipients.

FIG. 6 is an illustrative view of an Alerts screen. The system may send alerts relating to blood glucose readings and other medical test data as desired. An alert message may be sent to a designated person and email address as stored in the device and system. The alert may be sent via email or as an SMS message. The user may designate whether the blood glucose reading or score falls into one of the following categories of warnings: Warning Low, Warning High, Emergency Low, Emergency High so as to indicate to the recipient whether the user's blood glucose reading is a level to initiate action or diagnosis by a medical or health care provider such as a nurse or treating physician. The user may designate the frequency of the alert and designate the number of times the message is to be sent or expected to be sent in a given day or time period. A threshold limit may be designated such that an alert message is sent to the designated recipient if under this threshold amount. The alert can be sent for one or more patients or users and each patient or user can designate as many recipients as they choose as well as the frequency of alter messages to be sent.

FIG. 7 is an illustrative view of a Registration screen. Upon using the device and corresponding system, a user registers their device with the corresponding systems software. This includes the user's personal and medical information as well as their corresponding mobile and stationary devices. A user's mobile device's International Mobile Station Equipment Identity is recorded a unique identification number for GSM mobile phones.

Multiple devices per user can be registered which enables all of a specified user's devices to communicate wireless with one another. Devices can be updated and removed as necessary.

A Summary is below on the use of the apparatus and method of disclosed embodiments and how each of patients, healthcare providers, and insurance/financially interested parties can use and utilize disclosed embodiments. The system automatically sends glucose readings via text message, email or fax to family members, caregivers, physicians or other designees. For examples, if you require your blood glucose results to be released and transmitted two times a day to your doctor but three times a day to your nurse practitioner then the system allows for that. The system allows for multiple periods of sending to multiple designated users. The frequency of transmitting results can be adjusted depending on the user, healthcare provider and patient's needs. All data is stored on a website that can be accessed by the patient and whomever patient designates as an authorized user.

Data is collected and may be used for Medicare Part B Audits. Disclosed embodiments are compatible and compliant with "HL7," or Health Level 7, a format for exchanging patient health information to create patient registries. Health Level-7 or HL7 refers to a set of international standards for transfer of clinical and administrative data between software applications used by various healthcare providers. Data is collected and may be integrated into various online patient portals or other electronic medical record systems. Data can be pulled from the system and device and transmitted or pushed by the system to multiple Medical Data Platforms via an open application interface (API).

The system provides Greater control and understanding of a patient's diabetes. The system of disclosed embodiments automatically maintains logbooks and graphical/trend reports. The system provides real time results which leads to better glycemic control. The system enables automated diabetic supply reorder reminders. The system automatically creates electronic patient data required to comply with Medicaid/Medicare Part B Utilization Guidelines and justifies and documents reason for frequent prescribed diabetes testing. For healthcare providers, the system insures compliance and accuracy with patient glucose readings, improves care coordination and collaboration with no additional costs, allows for automatic and electronic record keeping eases case management; and provides detailed usage records for regulatory and reimbursement requirements. For insurers, the system potentially saves billions of dollars in healthcare costs stemming from improved patient care and fraud prevention, complements existing diabetes management programs, and provides efficient data management. Through the system's communication network, blood glucose readings are recorded in a central database which in turn communicates back to the device/apparatus with confirmation of receipt of the readings.

The device or apparatus may include a glucometer with unique added functionality to transmit the glucose readings. The device may use various transmission protocol means such as USSD message transmission technology, SMS technology or GPRS technology. Through these transmission protocols, messages and data are transmitted to a central database where the messages and data are stored. These multiple ways of communication ensure that no message or data record to and from the device is lost. Each system of communication acts as a backup for the other and is programmed to work if one system fails. Once readings and results are stored, a text message (via SMS) can be sent to pre-defined recipients and a corresponding web site application can display the information, run reports, issue alerts, create graphs and more.

This disclosure describes the communication functionality and the record layout to transmit the glucose reading information. The system and device automatically uploads your glucose readings. Such readings may be directed to a plurality of individuals as programed by the user. The device has the functionality of an accurate glucose reading device (including, but not limited to a configuration by which calibration for precision and accuracy is established and maintained), processes the reading correctly within the device, and prepares a record for transmission according to the impetus of embodiments as described herein.

The device's capabilities are critical to successful operation of device transmission, and are described in details in the "device architecture and specifications" document and as described in U.S. Patent Provisional Application No. 62/169,875 filed Jun. 2, 2015.

If there is no network coverage in the area, the device is constructed and configured to store the information within the device, and transmit the information the next time a reading is taken. In one embodiment, the device stores up to 100 unsent readings and be able to send them at later time. The device captures the local date and time from a global network, using a GSM module, and submits the date and time as part of the record layout. The device keeps the last reading successfully sent, and sends it again on the next transmission. This redundancy is to ensure no readings are missed. A central database checks and ensures that redundant records are not inserted into the database, by comparing new records to existing records already stored. The speed of the transmission depends on the local network in each location where the readings are taken. Each device has a GSM module incorporated therein. The device includes a subscriber identity module or subscriber identification module (SIM) card. A SIM card is an integrated circuit that is intended to securely store the international mobile subscriber identity (IMSI) and the related key used to identify and authenticate subscribers on mobile telephony devices (such as mobile phones and computers). The SIM card of the device, may be a physical SIM card or virtual SIM (a mobile phone number provided by a mobile network operator that does not require a physical SIM card to connect phone calls to a user's mobile phone) and is attached to a GSM module and communicates with the local networks. Once readings are sent from the device to the GSM module, the reading, or readings are transmitted to the network using the SIM card. The transmission is done by formatting a message with various lengths of 1 and up to 80 characters. The 80 characters limitation is to ensure that every network in the world can support the transmission. Each message must end with a special character that indicates end of transmission. Each record can carry up to four readings. Up to three of the readings are new and the fourth one is always a redundant reading of the last successful reading. See record layout below for further illustration. In another embodiment each record may contain additional records. However, to ensure redundancy, one of the records will be always be redundant while the remaining are new. In another embodiment, the device has a SIM card with 3 IMSIs.

Each device is constructed and configured with an indication pointer. The indication pointer will always point to the memory address of the last reading that was already sent successfully with a positive confirmation of receipt from the central database. In normal operation after a glucose measurement is recorded, both the new reading and the last reading will be sent immediately after the measurement. Subsequently, the pointer will be updated and point to the new memory address. In this case, two readings are sent via one message. The last reading is for a redundant verification and synchronization and should not be inserted into the central database. Redundant messages are automatically sent by the system.

If the transmissions failed for any reason, the unsent reading(s) are kept within the device and are configured to store a plurality of unsent readings. In one embodiment, the device is configured to keep up to 100 unsent readings. Once the connectivity is restored and upon a new measurement or reading, the unsent reading(s) will be sent. The transmission of unsent readings can be manual, automatic, or combinations thereof. The device is capable of storing records for a single user or for multiple user as would be common in a hospital or long term care facility setting.

If one to three readings were not sent, then the unsent reading(s) are sent together with the last reading already sent successfully before and stored in central database, for a total of maximum four readings in one message. After the message is sent and confirmed successfully, the pointer will be updated and point to the new last reading. The new last reading will become the last reading in next message. If more than three readings were not sent, the device will automatically repeat the process above and send several messages, until all readings are sent. The device will ensure that each message always has one redundant reading for synchronization.

The central database, upon successful completion of processing the incoming record, will reply with the message "success". The device, upon receiving this message, will display "OK" on the user screen, and will update the pointers as described above. The above message solution and redundancy process may use USSD messages as form of communication as well as GPRS, Short Text Message (SMS) method and Voice channels.

The record layout and the communication processes involved with sending glucose readings from a glucometer medical device according to disclosed embodiments, in one embodiment, is described herein below. For example, each record to be sent via a USSD message may contain up to 80 characters. The first 8 characters appear only on the first reading, while the rest of the readings in the record have only specific reading data. A color-coded record structure is as follows. Each color displays the unique characteristics of the field and the table below gives additional information on each field. In this example you can see a record with 2 readings, separated by comma (This example is illustrative only and does not limit the scope of actual devices and methods).

Example 1

U012345611012818341529900,11012818401589900#

| start | end | example | range | Description |
|---|---|---|---|---|
| 1 | 1 | U | 0~9, A~Z | Protocol Identification (U = USSD) |
| 2 | 2 | 0 | 0~9, A~Z | Customer Database Identification (if not used, set this character to zero) |
| 3 | 8 | 123456 | 000000~ 999999 | Device Identification (In future, this can be removed, and then use subscriber ID instead) |
| 9 | 10 | 11 | 10~99 | Year (2010~2099) |
| 11 | 12 | 01 | 01~12 | Month |
| 13 | 14 | 28 | 01~31 | Day |
| 15 | 16 | 18 | 00~23 | Hour (24 hours format) |
| 17 | 18 | 34 | 00~59 | Minutes |
| 19 | 21 | 152 | 000~999 | Sugar level |
| 22 | 23 | 99 | 00~99 | Battery strength in percentage (100% = 99%) |
| 24 | 24 | 0 | 0~9, A~Z | Event: Before Meal (0), After Meal (1), Control Solution Test (2), After Exercise (3), After Taking Medicine (4) . . . |
| 25 | 25 | 0 | | Future Use |
| 26 | 26 | , or # | , or # | Comma (,) to separate between records, pound sign (#) on the last record |

Length of each record:

| Header | Read 1 | Read 2 | Read 3 | Read 4 |
|---|---|---|---|---|
| 1 | | | | |
| 1 | | | | |
| 6 | | | | |
| | 2 | 2 | 2 | 2 |
| | 2 | 2 | 2 | 2 |
| | 2 | 2 | 2 | 2 |
| | 2 | 2 | 2 | 2 |
| | 2 | 2 | 2 | 2 |
| | 3 | 3 | 3 | 3 |
| | 2 | 2 | 2 | 2 |
| | 1 | 1 | 1 | 1 |
| | 1 | 1 | 1 | 1 |
| | 1 | 1 | 1 | 1 |
| 8 | 18 | 18 | 18 | 18 |

The communication between the device, server, and the web site central data base is done using XML commands. The device sends a message. The HLR changes it to XML command and transfers it to the server. The server sends the XML to the IP address of the web site. The web site processes the request, and generates a reply XML back to server. The server sends the XML to the HLR. The HLR changes the XML to USSD message and sends it to the device. The device displays the message on the screen as "OK" if it gets "success" or "ERR" if the return message is different.

EXAMPLES

Message sent to web site:
<mo-ussd-submit-request version="1.0"id="791">
<msisdn>19038904313</msisdn>
<userdata>U00008001108240702134700000000, 11082916007777700000#</user-data>
<imsi>310630803000351</imsi>
</mo-ussd-submit-request>

On successful processing, the web site will return to the server:
<user-data>successx</user-data>

On failure processing, the web site will return to the server:
<user-data>Invalid argument supplied</user-data>

Server return to device:
<user-data>successx</user-data> or <user-data>Invalid argument supplied</user-data>

In other embodiments, the Glucometer is configured with 2 way communication to send and receive USSD messages up to 140 characters long. USSD transmission is preferred for significant transmission advantages. Another embodiment contemplates using only 80 characters to comply with any network in the world. USSD is additionally preferred as messages are highly secured. However, the above example also works with GPRS and SMS method of message transmission.

Currently, as configured the device is functional with worldwide service in 200 countries and 600 2G networks. The device may also be configured for 4G and 3G wireless networks. Moreover, the device may be configured for 5G wireless networks, offering faster speeds and more reliable connections on smartphones and other devices than prior generations of cellular communication standards. In embodiments, the device may be configured for so-called CAT-M communications, the second generation of LTE chipsets meant for Internet of Things (IoT) applications, wherein the "M" stands for "machines." CAT-M enables reduced power consumption by capping speeds at 10 megabits per second, or even less.

The device is configured with automatic synchronization of local date/time. The device is configured with an automatic switch to adjust the device to "airplane mode" or sleep mode after sending messages or results in order to conserve the device's battery life. The device has manual ability to set different date formats and time formats. The time on the device may be set manually. Time may be synchronized on the device as well. The device may automatically change time zones based on where the user is located. The device's test strip turns the devices GSM capabilities on and off. The device is comprised of a full color 2.4" screen and is configured with an automatic screen shutdown to conserve energy. In another embodiment the device may be comprise a larger or smaller screen.

In one embodiment of the device, there are three test modes: before meal, after meal and control solution test. Blood glucose readings may be displayed either in mg/dl or milimol per litre (mmol/l). The unit has a single user mode and a multi user mode whereby the multi user supports up to 35 unique users or patients. The device may support multiple patient records in the same unit wherein all records may be stored on the device's SIM card or in the cloud storage system of the user or health care provider or where directed. The unit stores the last 1,000 reading records per patient/user up to a total of up to 35,000 records. The unit currently supports 6 built-in languages and is configurable to manufacture specification supporting up to 80 different languages with an automatic switch to local language of selected languages. The device currently supports the following languages: English, Arabic, Hebrew, Spanish, French, Hungarian, Chinese, Italian and Turkish. The device has a display for 7 digits for the device ID's, IMEI, IMSI and SIM tool kit. In another embodiment, the device may store a plurality of devices per patient/user. The device is configurable to select networks manually and for automatic network selection to be always on. The device may send mock alerts and tests in order to confirm proper transmission and is configurable to warn if errors in transmission occur. The device conducts a quick blood test in between about 0.5 to about 5 seconds. The device conducts a quick communication to indicate a successful recording of a user's blood glucose, up to 20 seconds to get a reply "Successfully Recorded."

For marketing purposes, the device is selectively configurable to display any one or combination of a customer specific logo, various advertising messages on screen, and the like. The device may contain an advertising module where product placement and advertisements may be featured while a glucose reading is being recorded or transmitted. The device is able to accommodate instant, directed and consumer personal advertisements. The system and device is marketed as the iGlucose® system and consists of the iGlucose® device (a glucometer) and an online diabetes management portal. iGlucose® uses machine-to-machine (M2M) cellular technology to facilitate wireless communication from areas with limited connectivity, and ensures you and your diabetes care team stay connected at all times. Blood glucose readings from your iGlucose® device are transmitted to a secure online database where you can access the data and share it in various graphic and tabular formats with pre-determined family members, caregivers, or healthcare professionals via email, text message, fax or by access to the web portal.

In one preferred embodiment, there is no action needed to transmit the data, i.e. no buttons to push, and a patient does not even have to remove the strip. The unit goes from blood test to data transmit automatically. In another embodiment, the system and device may interoperable with a variety of diabetic machines and devices such as insulin pumps, insulin pens, blood glucose software; diagnostic and medical devices for reading physical and bodily characteristics such as temperature via thermometers, blood pressure; and weight via scales.

Device Expansion Platform

The apparatus 100 meter may be supplemented with a docking station to which the apparatus 100 may be coupled. In embodiments, communication capabilities may by enhanced using Bluetooth Low Energy (BLE) (a/k/a Bluetooth Smart), or Near Field Communication (NFC) or the like for use with one or more other wireless devices. For example, such other wireless devices may include a scale that determined the user's body weight; a blood pressure (BP) cuff or monitor that determines the user's current blood pressure; a heart rate monitor that determined the user's heart rate; or other devices such as an insulin pen or oxygen dispenser, or the like. Such devices may be enabled to communicate with the docking station via wi-fi, BLE, NFC, radio frequency (RF) or other appropriate wireless communication technology.

Alternatively or in addition, embodiments may be partially implemented and/or enhanced by adding a so-called plug-in dongle to the system. In an embodiment, such a dongle may be plugged into the apparatus 100 to communicate a radio frequency ID (RFID) to an RF reader, for example, to convey testing results in an environment in which a plurality of apparatuses 100 are in operation, such as in a hospital environment. In embodiments, such a dongle may be inserted into a port of the apparatus 100, or a port of an intermediary communication device such as the docking station to which the apparatus 100 may be coupled, or a PC or the like set up as a communications server, for example. In embodiments, the apparatus 100 may require access to a dongle to provide some or all of the functionality described herein. Or, in embodiments a dongle may provide for encryption or other communications security measures.

In embodiments, aspects of the system may be used advantageously with a continuous glucose monitor (CGM) instead of a medical testing apparatus 132. A CGM is a device used for monitoring blood glucose on a continual basis. A CGM takes a reading at predetermined regular intervals using an electrode inserted under the user's skin and held in place by an adhesive. A transmitter attached to the electrode sends data to a separate receiver. For example, after insertion of glucose sensors in a user's subcutaneous tissue, the user may be provided access to their current glucose level by scanning the sensors with a suitable device.

In embodiments, biometric ID capabilities may be included in apparatus 100, or in a communicatively coupled docking station or PC, or the like. The ID may be used to secure access to apparatus 100. Such biometric ID may include sensors for determining one or more of a user's fingerprint, or eye scan; or facial or voice recognition, or the like.

In embodiments, software and firmware updates may be provided wirelessly to apparatus 100 using any appropriate over the air (OTA) technology.

In embodiments, apparatus 100 may include additional on-meter algorithms, typically implemented by a processor in apparatus 100 executing software stored in a memory of apparatus 100. These algorithms may include one or more of determining High/Low bG levels, time and/or duration bG is in range, and the like. Further, generating and sending alerts based on bG values, determining bG trends, and calculating appropriate insulin dosing may be provided.

In embodiments, apparatus 100 may additionally include an A1c estimator function, that estimates A1c from a series of bG measurements by any means known in the art. Glycated hemoglobin (hemoglobin A1c) covalently bonds to glucose. Thus, A1c can be used as a diagnostic test for blood sugar, and hence diabetes. In an example, A1c measures have been standardized against bG measurements using the results of large scale trials. For example, a trial conducted in 1993 called the Diabetes Control and Complications Trial (DCCT) determined A1c values can be estimated from estimated average glucose (eAG) measurements as $$A1c\ (\%) \approx (eAG(mg/dl)+46.7)/28.7.$$

The eAG in turn can be calculated from the stored history of measured bG levels, and can be used in the foregoing equation to estimate A1c. Accordingly, the A1c estimator function of apparatus 100 may use stored bG measurements to estimate A1c in accordance with this equation, although other studies' results may additionally or alternatively be used, and/or other models known in the art for determining A1c from bG measurements may be used.

In embodiments, apparatus 100 may include an A1c meter that analytically measures A1c in a blood sample in addition to or as an alternative to a bG meter. Such an A1c meter may use any appropriate handheld technology known in the art.

In embodiments, two-way communication capabilities may be customized, for example, using personal information stored in a user profile.

Referring now to FIGS. 8-14, there is an exemplary apparatus 100 shown in a number of views. The apparatus 100 is shown from a perspective view, front view, back view, left side view, right side view, top view, and a bottom view, respectively. As shown, apparatus 100 generally has an external housing 101, at least one touch sensitive button 102, a display 105, a charging indicator or light 122, a receptacle 124, a charging port 126, a sound emitting device 128, and a slidable member 130.

The display 105 is a visual display that may interface with the sound emitting device 128, such as a speaker(s), to create an audiovisual experience for the user. Preferably, the display 105 is a liquid crystal display (LCD), however, other displays including those containing light emitting diodes and organic light emitting diodes which may be enhanced with quantum dot technology. In some embodiments, it is preferable that the display 105 be touch sensitive. In yet other embodiments, the touch sensitive buttons 102 are used to navigate the menu trees and generally operate the device as a whole. In other embodiments, a combination of touch sensitive screens and buttons may be implemented.

Figure 9:
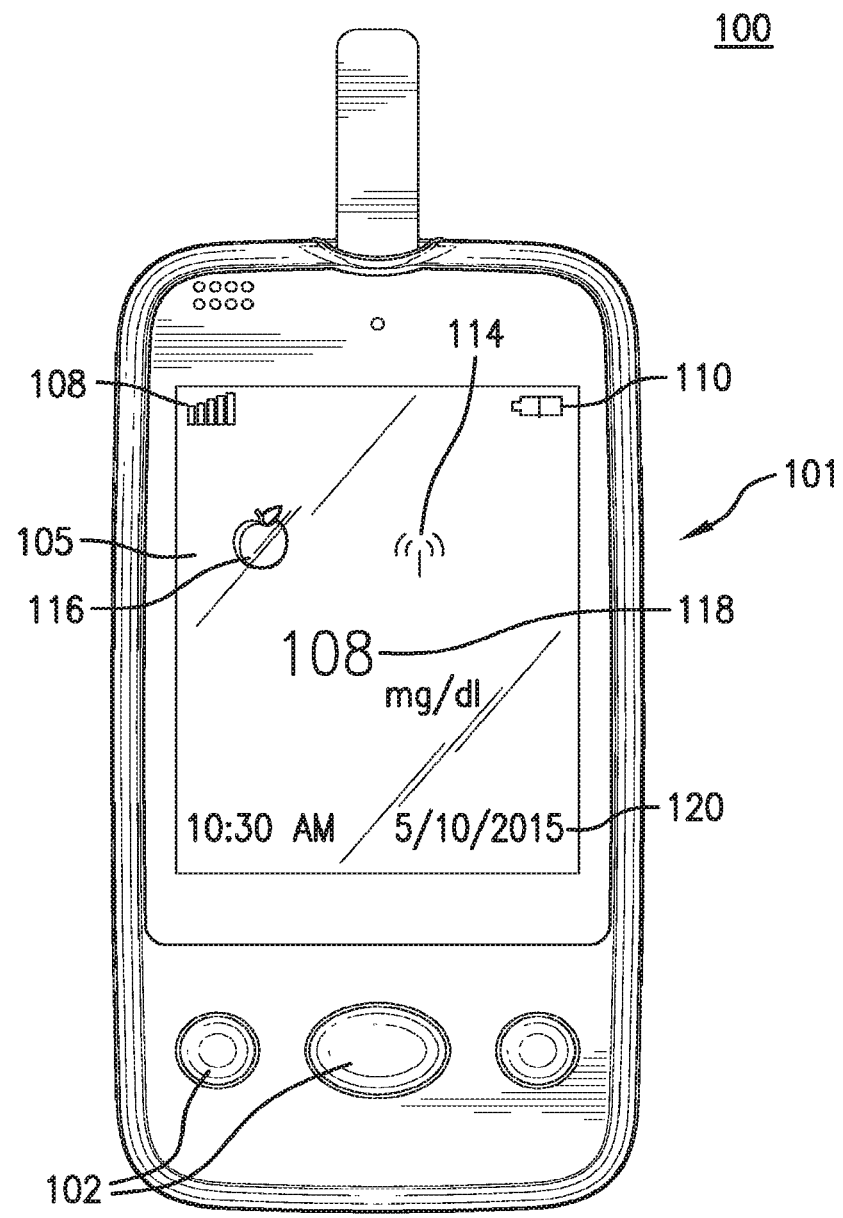
FIG. 9 is a front view of an embodiment in accordance with the disclosure.
Figure 10:
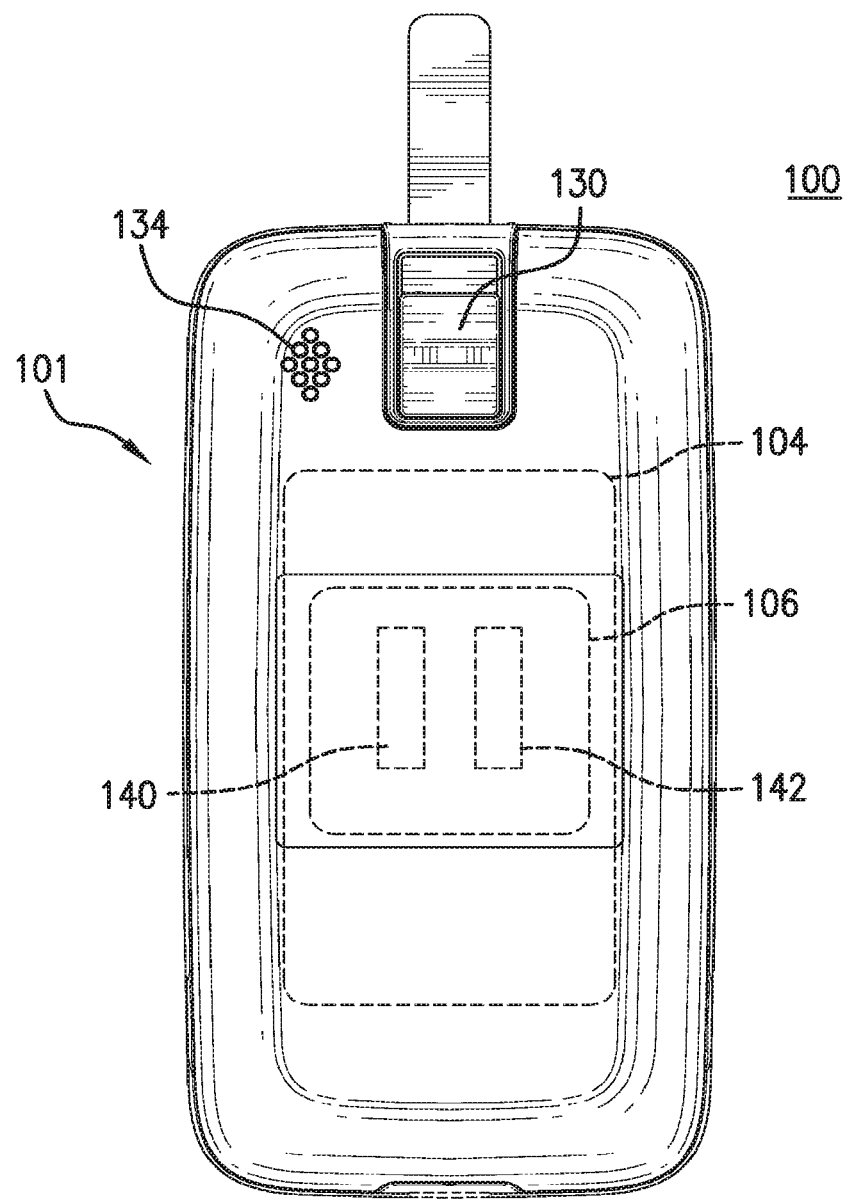
FIG. 10 is a back view of an embodiment in accordance with the disclosure.
Figure 13:
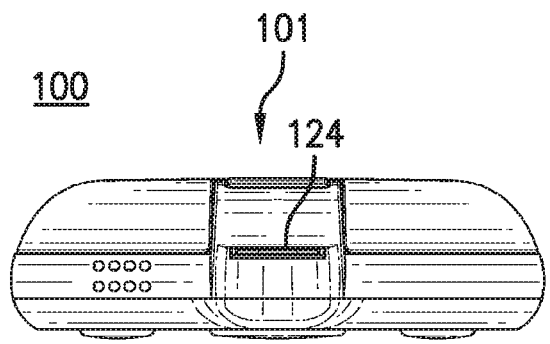
FIG. 13 is a top view of an embodiment in accordance with the disclosure.
Figure 14:
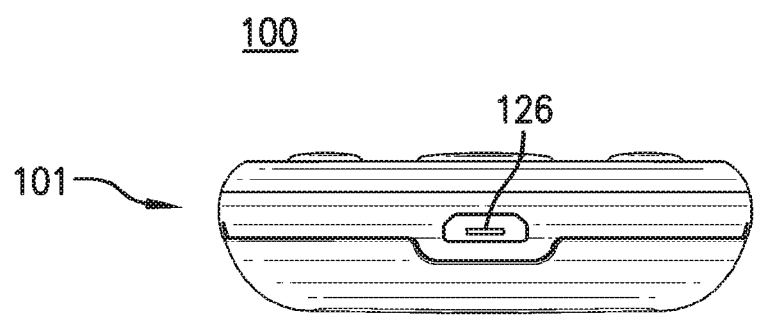
FIG. 14 is a bottom view of an embodiment in accordance with the disclosure.

The display 105 further has outputs, as shown in FIG. 9, corresponding to various functionality such as a signal strength indicator 108, battery meter 110, standby mode indicator 112, a sending signal indicator 114, a mode indicator 116, a test output value 118, and the date and time 120 of the location of the apparatus. As described above, the touch sensitive buttons 102 can be used to interact with or change any part of the display 105.

The signal strength indicator 108 gives a user a visual representation of the afforded strength of a cellular communications signal such as a global system for mobile communications (GSM). The signal strength indicator 108 may be represented by a varying number of bars or lines based on the strength of the signal received by the apparatus 100. This connection enables the automatic transmission of the medical test results upon completion of at least one medical test. If there is no network coverage in the area, the apparatus 100 is constructed and configured to store the information within the apparatus 100 via the memory 140 contained therein. The information can then be automatically transmitted the next time a reading is taken or coverage becomes available. In one embodiment, the apparatus 100 stores up to 100 unsent readings to be sent at a later time. When the information is sent, the apparatus 100 also sends a time stamp (including the date) for record keeping purposes.

In some embodiments, each apparatus 100 has a GSM module incorporated therein. A SIM card, either physical SIM or virtual SIM, is attached to a GSM module and communicates with the local network. Once readings are sent from the device to the GSM module, the reading, or readings are transmitted to the network using the SIM card.

The battery meter 110 provides a visual cue as to the remaining battery level. Once a certain threshold has been passed an alert may be generated and battery meter 110 may change color. The battery may be recharged using a recharging apparatus which can be coupled to the charging port 126 located on the bottom of the apparatus 100. When the battery is recharging, a charging light 122 may appear. Once the charging has completed, this charging light 122 may change color or no longer appear.

A sending signal indicator 114 signifies that a signal has been sent from an apparatus 100 to a remote location upon the completion of a medical test. The mode indicator 116 indicates the operational mode of the apparatus 100 which may correspond to the type of test to be performed or the timing of the test to be performed. The test output value 118 is a visual indication of a result of at least one medical test performed with the apparatus 100. The date and time 120 simply show the user the date and time of their location to ensure they remain on schedule for testing purposes as well as time stamping test results.

The external housing 101 is preferably comprised of at least an upper half and a lower half with the upper half being coupled to the lower half defining a space therebetween. The upper half may be separable from the lower half via tabs 144 as shown in FIGS. 11-12. This space defined by the external housing 101 houses at least the power source or battery 104, processor 106, and memory 140. The processor 106 contains instructions thereon for executing at least one program directed towards medical testing and its applications. Further, once the medical test has been completed, the results are stored in the memory 140 and automatically sent to a remote location, such as a server or doctor's office or the like, via a wireless transceiver 142. The medical test results may be sent via SMS, email, fax, and the like or some combination thereof.

The external housing 101 provides for a receptacle 124 and a charging port 126. The charging port 126, as described above, enables a charging apparatus to be employed to recharge the power source or battery 104 of the apparatus 100.

The receptacle 124 enables a medical testing apparatus 132 to be inserted therein. The medical testing apparatus 132 takes many forms and in some instances may be a strip for testing blood glucose levels. Such a strip is generally known in the art and contains a first end having an electrical connector capable of establishing an operable electronic connection with the apparatus 100. The opposing end of the strip may have an area to receive a bodily fluid such as blood. The bodily fluid causes a reaction in the strip which is measured by the apparatus 100. In other embodiments, other types of testing may be employed. Further, the medical testing apparatus 132 may also take other forms. Once the medical test has been completed, the slidable member 130 is used to eject the medical testing apparatus 132.

At least one embodiment and its technical specifications and associated hardware are described in the table below.

TABLE 1

| | Main | Sub | Details |
|---|---|---|---|
| Hardware | | | |
| GSM | GSM Platform | | MT6260 |
| | Mode | | GSM + GPRS+ USSD |
| | Frequency | | GSM 850/900/1800/1900 |
| | Antenna | | Interior on the bottom |
| Glucose | Type | | Module mounted |
| | IC | | NEC 78F0593 |
| | Test Sample | | Fresh capillary whole blood |
| | Test Result. | | Plasma/Serum glucose |
| | Sample Size | | Less than 0.5 µL |
| | Measuring Time | | Less than 5 seconds |
| | Measuring Range | | 20-600 mg/dL (1.1-33.3 mmol/L) |
| | Hematocrit Range | | 30%-55% |
| | Operating Temp. Range | | 10° C.-40° C. (50° F.-104° F.) |
| | Operating Relative Humidity | | 10%-90% RH |
| | Storage/transport Temp. Range | | 0° C.-50° C. (32° F.-122° F.) |
| | Storage/transport Relative Humidity | | 10%-90% RH |
| | Atmospheric pressure | | 700-1060 hPa |
| General | LCM | Size | 2.4" QVGA |
| | | Nature | Hi contrast TFT |
| | | Colors | 260K |
| | | Resolution | 320 * 240 pixels |
| | Button pad (3 Buttons) | Left button | Menu, information menu |
| | | Middle button | ON/OFF; Enter, test mode change |
| | | Right button | Averages, readings. history |
| | Dimension | | 100 * 50 * 15 mm |
| | Port | | Micro-USB Charging, software download |
| | Speaker | | 15 mm mini-speaker as buzzer or vocal reminding |
| | Battery | Capacity | 3.7 V, 1,000 mAh Li-Ion |
| | | Last time | 25-30 days for normal use (2-3 tests per day) |
| Accessory | Wall Charger | Adapter | Shenzhen Samson Power Technology Model : S0S0-050-US AC input: 100-240 VAC, 50/60 Hz, 0.2A; DC output: 5 V, 0.5A |
| | | USB cable | Micro SP, 100 cm |
| Software functions | | | |
| | Data entry | Storage | 1,000 entries per user, up to 35 users |
| | Main standby page | | GSM signal strength, battery level, carrier name, date/time etc. |
| | Message | Yes | Server can send to SGM-03, for any tips, feedbacks etc. |
| | Alarm | Yes | 5 items |
| | GPRS/USSD | Yes | GPM Class1.2 |
| | Languages | | English, French, Spanish, Hungarian, Arabic, Hebrew and Chinese by default. |

The apparatus shown and described is suitable for blood glucose testing, however a similar apparatus suitable for A1c analysis (not shown) may be substantially similar in form and function. For example, a user may obtain a sample of their own blood, prepare the sample, insert the prepared sample into apparatus 100 for analysis, apparatus 100 may analyze the sample and automatedly send information of the analyzed sample via a cellular communication to a remote device for storage, data analysis, messaging, and the like. In addition or alternatively, the apparatus 100 and/or a remote server or other device may access stored bG information and analyze it to derive an estimated A1c value. This may be done upon request of the user, or may be performed automatically in accordance with a preset schedule. In embodiments, messaging based on the result may be automatedly initiated.

In order to use an embodiment of the apparatus described herein or others thereof, a user preferably completes a series of steps, of which not all will be required nor are the steps necessarily required to be completed in the manner/order as described.

A user first needs to create a user account to be associated with the particular apparatus. Such an account may be created with a web/mobile application or website or other electronic programming option. Once an account has been created and, in some instance user verified, a user can then modify their account and user profile as necessary including adding, editing, and deleting information. In order to properly associate with the apparatus in question, if a user receives a new apparatus, then they must update their profile with the specific apparatus information such as serial number and other unique apparatus identifiers. From their account and profile, a user can also set alerts to be directed in the event of an abnormal or other reading that may comprise the user's health, add or change apparatus associated the with account, and perform various other functions associated with the apparatus.

In order to complete a medical test, such as a glucose blood test, a user may follow the following steps. First, a user should wash their hands in warm water using soap and rinse and dry completely.

Second, the user should select the appropriate test mode: "Before Meal" or "After Meal." This can be done either by using the touch sensitive buttons. An icon will be displayed on the display to indicate the selection made: "Before Meal" shows, for example, a whole apple icon, "After Meal" shows, for example, a partially eaten apple icon. If the test is performed within about two hours after a meal, use the "After Meal" setting, otherwise, the user would typically use the "Before Meal" setting.

Third, a user should remove a new test strip from a vial, and replace the vial cap tightly after removing the test strip.

Fourth, the user should use a safety lancet or lancing device to prick at least one finger and draw a drop of blood.

Fifth, the test strip should be inserted, usually with the arrow side facing up, into the strip slot of the device. A message such as "Strip Inserted" and then "Apply a Drop of Blood" may appear on the display. The user should check that the code number on the meter matches the code on the vial. If the two numbers match, the user may begin blood testing. Otherwise the user should insert a new strip.

Sixth, hold the device and apply a drop of blood to the top front of the test strip, where several stripes are visible. The test result will show in about five seconds and a "Glucose Value" number, or test results, appears on the display. After a few more seconds, the sending signal icon blinks on the display as the test result is transmitted to the online database, remote location, doctor, etc. A message such as "Successfully Recorded" may subsequently appear on the display. This transmission occurs automatically and requires no undue input or steps from the user.

Systems, Devices and Operating Systems

Typically, a user or users, which may be people or groups of users and/or other systems, may engage information technology systems (e.g., computers) to facilitate operation of the system and information processing. In turn, computers employ processors to process information and such processors may be referred to as central processing units (CPU). One form of processor is referred to as a microprocessor. CPUs use communicative circuits to pass binary encoded signals acting as instructions to enable various operations. These instructions may be operational and/or data instructions containing and/or referencing other instructions and data in various processor accessible and operable areas of memory (e.g., registers, cache memory, random access memory, etc.). Such communicative instructions may be stored and/or transmitted in batches (e.g., batches of instructions) as programs and/or data components to facilitate desired operations. These stored instruction codes, e.g., programs, may engage the CPU circuit components and other motherboard and/or system components to perform desired operations. One type of program is a computer operating system, which may be executed by CPU on a computer; the operating system enables and facilitates users to access and operate computer information technology and resources. Some resources that may be employed in information technology systems include: input and output mechanisms through which data may pass into and out of a computer; memory storage into which data may be saved; and processors by which information may be processed. These information technology systems may be used to collect data for later retrieval, analysis, and manipulation, which may be facilitated through a database program. These information technology systems provide interfaces that allow users to access and operate various system components.

Embodiments may be connected to and/or communicate with entities such as, but not limited to: one or more users from user input devices; peripheral devices; an optional cryptographic processor device; and/or a communications network. For example, disclosed embodiments may be connected to and/or communicate with users, operating client device(s), including, but not limited to, personal computer(s), server(s) and/or various mobile device(s) including, but not limited to, cellular telephone(s), smartphone(s) (e.g., iPhone®, Blackberry®, Android OS-based phones etc.), tablet computer(s) (e.g., Apple iPad™, HP Slate™, Motorola Xoomm™, etc.), eBook reader(s) (e.g., Amazon Kindlem™, Barnes and Noble's Nook™ eReader, etc.), laptop computer(s), notebook(s), netbook(s), gaming console(s) (e.g., XBOX Live™, Nintendo® DS, Sony PlayStation® Portable, etc.), portable scanner(s) and/or the like.

Networks are commonly thought to comprise the interconnection and interoperation of clients, servers, and intermediary nodes in a graph topology. It should be noted that the term "server" as used throughout this application refers generally to a computer, other device, program, or combination thereof that processes and responds to the requests of remote users across a communications network. Servers serve their information to requesting "clients." The term "client" as used herein refers generally to a computer, program, other device, user and/or combination thereof that is capable of processing and making requests and obtaining and processing any responses from servers across a communications network. A computer, other device, program, or combination thereof that facilitates, processes information and requests, and/or furthers the passage of information from a source user to a destination user is commonly referred to as a "node." Networks are generally thought to facilitate the transfer of information from source points to destinations. A node specifically tasked with furthering the passage of information from a source to a destination is commonly called a "router." There are many forms of networks such as Local Area Networks (LANs), Pico networks, Wide Area Networks (WANs), Wireless Networks (WLANs), etc. For example, the Internet is generally accepted as being an interconnection of a multitude of networks whereby remote clients and servers may access and interoperate with one another.

Disclosed embodiments may be based on computer systems that may comprise, but are not limited to, components such as: a computer systemization connected to memory.

Computer Systemization

A computer systemization may comprise a clock, central processing unit ("CPU(s)" and/or "processor(s)" (these terms are used interchangeable throughout the disclosure unless noted to the contrary)), a memory (e.g., a read only memory (ROM), a random access memory (RAM), etc.), and/or an interface bus, and most frequently, although not necessarily, are all interconnected and/or communicating through a system bus on one or more (mother)board(s) having conductive and/or otherwise transportive circuit pathways through which instructions (e.g., binary encoded signals) may travel to effect communications, operations, storage, etc. Optionally, the computer systemization may be connected to an internal power source; e.g., optionally the power source may be internal. Optionally, a cryptographic processor and/or transceivers (e.g., ICs) may be connected to the system bus. In another embodiment, the cryptographic processor and/or transceivers may be connected as either internal and/or external peripheral devices via the interface bus I/O. In turn, the transceivers may be connected to antenna(s), thereby effectuating wireless transmission and reception of various communication and/or sensor protocols, for example the antenna(s) may connect to: a Texas Instruments WiLink WL1283 transceiver chip (e.g., providing 802.1 in, Bluetooth 3.0, FM, global positioning system (GPS) (thereby allowing the controller to determine its location)); Broadcom BCM4329FKUBG transceiver chip (e.g., providing 802.11 In, Bluetooth 2.1+EDR, FM, etc.); a Broadcom BCM4750IUB8 receiver chip (e.g., GPS); an Infineon Technologies X-Gold 618-PMB9800 (e.g., providing 2G/3G HSDPA/HSUPA communications); and/or the like. The system clock typically has a crystal oscillator and generates a base signal through the computer systemization's circuit pathways. The clock is typically coupled to the system bus and various clock multipliers that will increase or decrease the base operating frequency for other components interconnected in the computer systemization. The clock and various components in a computer systemization drive signals embodying information throughout the system. Such transmission and reception of instructions embodying information throughout a computer systemization may be commonly referred to as communications. These communicative instructions may further be transmitted, received, and the cause of return and/or reply communications beyond the instant computer systemization to: communications networks, input devices, other computer systemizations, peripheral devices, and/or the like. Of course, any of the above components may be connected directly to one another, connected to the CPU, and/or organized in numerous variations employed as exemplified by various computer systems.

The CPU comprises at least one high-speed data processor adequate to execute program components for executing user and/or system-generated requests. Often, the processors themselves will incorporate various specialized processing units, such as, but not limited to: integrated system (bus) controllers, memory management control units, floating point units, and even specialized processing sub-units like graphics processing units, digital signal processing units, and/or the like. Additionally, processors may include internal fast access addressable memory, and be capable of mapping and addressing memory beyond the processor itself; internal memory may include, but is not limited to: fast registers, various levels of cache memory (e.g., level 1, 2, 3, etc.), RAM, etc. The processor may access this memory through the use of a memory address space that is accessible via instruction address, which the processor can construct and decode allowing it to access a circuit path to a specific memory address space having a memory state. The CPU may be a microprocessor such as: AMD's Athlon, Duron and/or Opteron; ARM's application, embedded and secure processors; IBM and/or Motorola's DragonBall and PowerPC; IBM's and Sony's Cell processor; Intel's Celeron, Core (2) Duo, Itanium, Pentium, Xeon, and/or XScale; and/or the like processor(s). The CPU interacts with memory through instruction passing through conductive and/or transportive conduits (e.g., (printed) electronic and/or optic circuits) to execute stored instructions (i.e., program code) according to conventional data processing techniques. Such instruction passing facilitates communication within disclosed embodiments and beyond through various interfaces. Should processing requirements dictate a greater amount speed and/or capacity, distributed processors (e.g., Distributed embodiments), mainframe, multi-core, parallel, and/or super-computer architectures may similarly be employed. Alternatively, should deployment requirements dictate greater portability, smaller Personal Digital Assistants (PDAs) may be employed.

Depending on the particular implementation, features may be achieved by implementing a microcontroller such as CAST's R8051XC2 microcontroller; Intel's MCS 51 (i.e., 8051 microcontroller); and/or the like. Also, to implement certain features of the various embodiments, some feature implementations may rely on embedded components, such as: Application-Specific Integrated Circuit ("ASIC"), Digital Signal Processing ("DSP"), Field Programmable Gate Array ("FPGA"), and/or the like embedded technology. For example, any of the component collection (distributed or otherwise) and/or features may be implemented via the microprocessor and/or via embedded components; e.g., via ASIC, coprocessor, DSP, FPGA, and/or the like. Alternately, some embodiments may be implemented with embedded components that are configured and used to achieve a variety of features or signal processing.

Depending on the particular implementation, the embedded components may include software solutions, hardware solutions, and/or some combination of both hardware/software solutions. For example, features discussed herein may be achieved through implementing FPGAs, which are a semiconductor devices containing programmable logic components called "logic blocks", and programmable interconnects, such as the high performance FPGA Virtex series and/or the low cost Spartan series manufactured by Xilinx. Logic blocks and interconnects can be programmed by the customer or designer, after the FPGA is manufactured, to implement any of the features of disclosed embodiments. A hierarchy of programmable interconnects allow logic blocks to be interconnected as needed by the system designer/administrator, somewhat like a one-chip programmable breadboard. An FPGA's logic blocks can be programmed to perform the function of basic logic gates such as AND, and XOR, or more complex combinational functions such as decoders or simple mathematical functions. In most FPGAs, the logic blocks also include memory elements, which may be simple flip-flops or more complete blocks of memory. In some circumstances, disclosed embodiments may be developed on regular FPGAs and then migrated into a fixed version that more resembles ASIC implementations. Alternate or coordinating implementations may migrate features of the controller to a final ASIC instead of or in addition to FPGAs. Depending on the implementation all of the aforementioned embedded components and microprocessors may be considered the "CPU" and/or "processor" for the present ivention.

Power Source

The power source may be of any standard form for powering small electronic circuit board devices such as the following power cells: alkaline, lithium hydride, lithium ion, lithium polymer, nickel cadmium, solar cells, and/or the like. Other types of AC or DC power sources may be used as well. In the case of solar cells, in one embodiment, the case provides an aperture through which the solar cell may capture photonic energy. The power cell is connected to at least one of the interconnected subsequent components of the present ivention thereby providing an electric current to all subsequent components. In one example, the power source is connected to the system bus component. In an alternative embodiment, an outside power source is provided through a connection across the I/O interface. For example, a USB and/or IEEE 1394 connection carries both data and power across the connection and is therefore a suitable source of power.

Interface Adapters

Interface bus(ses) may accept, connect, and/or communicate to a number of interface adapters, conventionally although not necessarily in the form of adapter cards, such as but not limited to: input output interfaces (I/O), storage interfaces, network interfaces, and/or the like. Optionally, cryptographic processor interfaces similarly may be connected to the interface bus. The interface bus provides for the communications of interface adapters with one another as well as with other components of the computer systemization. Interface adapters are adapted for a compatible interface bus. Interface adapters conventionally connect to the interface bus via a slot architecture. Conventional slot architectures may be employed, such as, but not limited to: Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and/or the like.

Storage interfaces may accept, communicate, and/or connect to a number of storage devices such as, but not limited to: storage devices, removable disc devices, and/or the like. Storage interfaces may employ connection protocols such as, but not limited to: (Ultra) (Serial) Advanced Technology Attachment (Packet Interface) ((Ultra) (Serial) ATA(PI)), (Enhanced) Integrated Drive Electronics ((E)IDE), Institute of Electrical and Electronics Engineers (IEEE) 1394, fiber channel, Small Computer Systems Interface (SCSI), Universal Serial Bus (USB), and/or the like.

Network interfaces may accept, communicate, and/or connect to a communications network. Through a communications network, the controller is accessible through remote clients (e.g., computers with web browsers) by users. Network interfaces may employ connection protocols such as, but not limited to: direct connect, Ethernet (thick, thin, twisted pair 10/100/1000 Base T, and/or the like), Token Ring, wireless connection such as IEEE 802. 11a-x, and/or the like. Should processing requirements dictate a greater amount speed and/or capacity, distributed network controllers (e.g., Distributed embodiments of the present invention), architectures may similarly be employed to pool, load balance, and/or otherwise increase the communicative bandwidth required by the controller. A communications network may be any one and/or the combination of the following: a direct interconnection; the Internet; a Local Area Network (LAN); a Metropolitan Area Network (MAN); an Operating Missions as Nodes on the Internet (OMNI); a secured custom connection; a Wide Area Network (WAN); a wireless network (e.g., employing protocols such as, but not limited to a Wireless Application Protocol (WAP), I-mode, and/or the like); and/or the like. A network interface may be regarded as a specialized form of an input output interface. Further, multiple network interfaces may be used to engage with various communications network types. For example, multiple network interfaces may be employed to allow for the communication over broadcast, multicast, and/or unicast networks.

Input Output interfaces (I/O) may accept, communicate, and/or connect to user input devices, peripheral devices, cryptographic processor devices, and/or the like. I/O may employ connection protocols such as, but not limited to: audio: analog, digital, monaural, RCA, stereo, and/or the like; data: Apple Desktop Bus (ADB), IEEE 1394a-b, serial, universal serial bus (USB); infrared: joystick; keyboard; midi; optical; PC AT; PS/2; parallel; radio; video interface: Apple Desktop Connector (ADC), BNC, coaxial, component, composite, digital, Digital Visual Interface (DVI), high-definition multimedia interface (HDMI), RCA, RF antennae, S-Video, VGA, and/or the like; wireless transceivers: 802.11a/b/g/n/x; Bluetooth; cellular (e.g., code division multiple access (CDMA), high speed packet access (HSPA(+)), high-speed downlink packet access (HSDPA), global system for mobile communications (GSM), long term evolution (LTE), WiMax, etc.); and/or the like. One typical output device may include a video display, which typically comprises a Cathode Ray Tube (CRT) or Liquid Crystal Display (LCD) based monitor with an interface (e.g., DVI circuitry and cable) that accepts signals from a video interface, may be used. The video interface composites information generated by a computer systemization and generates video signals based on the composited information in a video memory frame. Another output device is a television set, which accepts signals from a video interface. Typically, the video interface provides the composited video information through a video connection interface that accepts a video display interface (e.g., an RCA composite video connector accepting an RCA composite video cable; a DVI connector accepting a DVI display cable, etc.).

User input devices often are a type of peripheral device (see below) and may include: card readers, dongles, finger print readers, gloves, graphics tablets, joysticks, keyboards, microphones, mouse (mice), remote controls, retina readers, touch screens (e.g., capacitive, resistive, etc.), trackballs, trackpads, sensors (e.g., accelerometers, ambient light, GPS, gyroscopes, proximity, etc.), styluses, and/or the like.

Peripheral devices, such as other components of the cooling chest system, including temperature sensors, ice dispensers (if provided) and the like may be connected and/or communicate to I/O and/or other facilities of the like such as network interfaces, storage interfaces, directly to the interface bus, system bus, the CPU, and/or the like. Peripheral devices may be external, internal and/or part of the controller. Peripheral devices may also include, for example, an antenna, audio devices (e.g., line-in, line-out, microphone input, speakers, etc.), cameras (e.g., still, video, webcam, etc.), drive motors, ice maker, lighting, video monitors and/or the like.

Cryptographic units such as, but not limited to, microcontrollers, processors, interfaces, and/or devices may be attached, and/or communicate with the controller. A MC68HC16 microcontroller, manufactured by Motorola Inc., may be used for and/or within cryptographic units. The MC68HC16 microcontroller utilizes a 16-bit multiply-and-accumulate instruction in the 16 MHz configuration and requires less than one second to perform a 512-bit RSA private key operation. Cryptographic units support the authentication of communications from interacting agents, as well as allowing for anonymous transactions. Cryptographic units may also be configured as part of CPU. Equivalent microcontrollers and/or processors may also be used. Other commercially available specialized cryptographic processors include: the Broadcom's CryptoNetX and other Security Processors; nCipher's nShield, SafeNet's Luna PCI (e.g., 7100) series; Semaphore Communications' 40 MHz Roadrunner 184; Sun's Cryptographic Accelerators (e.g., Accelerator 6000 PCIe Board, Accelerator 500 Daughtercard); Via Nano Processor (e.g., L2100, L2200, U2400)

line, which is capable of performing 500+MB/s of cryptographic instructions; VLSI Technology's 33 MHz 6868; and/or the like.

Memory

Generally, any mechanization and/or embodiment allowing a processor to affect the storage and/or retrieval of information is regarded as memory. However, memory is a fungible technology and resource, thus, any number of memory embodiments may be employed in lieu of or in concert with one another. It is to be understood that the controller and/or a computer systemization may employ various forms of memory. For example, a computer systemization may be configured wherein the functionality of on-chip CPU memory (e.g., registers), RAM, ROM, and any other storage devices are provided by a paper punch tape or paper punch card mechanism; of course such an embodiment would result in an extremely slow rate of operation. In a typical configuration, memory will include ROM, RAM, and a storage device. A storage device may be any conventional computer system storage. Storage devices may include a drum; a (fixed and/or removable) magnetic disk drive; a magneto-optical drive; an optical drive (i.e., Blu-eray, CD ROM/RAM/Recordable (R)/ReWritable (RW), DVD R/RW, HD DVD R/RW etc.); an array of devices (e.g., Redundant Array of Independent Disks (RAID)); solid state memory devices (USB memory, solid state drives (SSD), etc.); other processor-readable storage mediums; and/or other devices of the like. Thus, a computer systemization generally requires and makes use of memory.

Component Collection

The memory may contain a collection of program and/or database components and/or data such as, but not limited to: operating system component(s) (operating system); information server component(s) (information server); user interface component(s) (user interface); Web browser component(s) (Web browser); database(s); mail server component(s); mail client component(s); cryptographic server component(s) (cryptographic server) and/or the like (i.e., collectively a component collection). These components may be stored and accessed from the storage devices and/or from storage devices accessible through an interface bus. Although non-conventional program components such as those in the component collection, typically, are stored in a local storage device, they may also be loaded and/or stored in memory such as: peripheral devices, RAM, remote storage facilities through a communications network, ROM, various forms of memory, and/or the like.

Operating System

The operating system component is an executable program component facilitating the operation of the controller. Typically, the operating system facilitates access of I/O, network interfaces, peripheral devices, storage devices, and/or the like. The operating system may be a highly fault tolerant, scalable, and secure system such as: Apple Macintosh OS X (Server); AT&T Plan 9; Be OS; Unix and Unix-like system distributions (such as AT&T's UNIX; Berkley Software Distribution (BSD) variations such as FreeBSD, NetBSD, OpenBSD, and/or the like; Linux distributions such as Red Hat, Ubuntu, and/or the like); and/or the like operating systems. However, more limited and/or less secure operating systems also may be employed such as Apple Macintosh OS, IBM OS/2, Microsoft DOS, Microsoft Windows 2000/2003/3.1/95/98/CE/Millennium/NTNista/XP (Server), Palm OS, and/or the like. The operating system may be one specifically optimized to be run on a mobile computing device, such as iOS, Android, Windows Phone, Tizen, Symbian, and/or the like. An operating system may communicate to and/or with other components in a component collection, including itself, and/or the like. Most frequently, the operating system communicates with other program components, user interfaces, and/or the like. For example, the operating system may contain, communicate, generate, obtain, and/or provide program component, system, user, and/or data communications, requests, and/or responses. The operating system, once executed by the CPU, may enable the interaction with communications networks, data, I/O, peripheral devices, program components, memory, user input devices, and/or the like. The operating system may provide communications protocols that allow the controller to communicate with other entities through a communications network. Various communication protocols may be used by the controller as a subcarrier transport mechanism for interaction, such as, but not limited to: multicast, TCP/IP, UDP, unicast, and/or the like.

Information Server

An information server component is a stored program component that is executed by a CPU. The information server may be a conventional Internet information server such as, but not limited to Apache Software Foundation's Apache, Microsoft's Internet Information Server, and/or the like. The information server may allow for the execution of program components through facilities such as Active Server Page (ASP), ActiveX, (ANSI) (Objective-) C (++), C# and/or .NET, Common Gateway Interface (CGI) scripts, dynamic (D) hypertext markup language (HTML), FLASH, Java, JavaScript, Practical Extraction Report Language (PERL), Hypertext Pre-Processor (PHP), pipes, Python, wireless application protocol (WAP), WebObjects, and/or the like. The information server may support secure communications protocols such as, but not limited to, File Transfer Protocol (FTP); HyperText Transfer Protocol (HTTP); Secure Hypertext Transfer Protocol (HTTPS), Secure Socket Layer (SSL), messaging protocols (e.g., America Online (AOL) Instant Messenger (AIM), Application Exchange (APEX), ICQ, Internet Relay Chat (IRC), Microsoft Network (MSN) Messenger Service, Presence and Instant Messaging Protocol (PRIM), Internet Engineering Task Force's (IETF's) Session Initiation Protocol (SIP), SIP for Instant Messaging and Presence Leveraging Extensions (SIMPLE), open XML-based Extensible Messaging and Presence Protocol (XMPP) (i.e., Jabber or Open Mobile Alliance's (OMA's) Instant Messaging and Presence Service (IMPS)), Yahcoo! Instant Messenger Service, and/or the like. The information server provides results in the form of Web pages to Web browsers, and allows for the manipulated generation of the Web pages through interaction with other program components. After a Domain Name System (DNS) resolution portion of an HTTP request is resolved to a particular information server, the information server resolves requests for information at specified locations on the controller based on the remainder of the HTTP request. For example, a request such as http://123.124.125.126/myInformation.html might have the IP portion of the request "123.124.125.126" resolved by a DNS server to an information server at that IP address; that information server might in turn further parse the http request for the "/myInformation.html" portion of the request and resolve it to a location in memory containing the information "myInformation.html." Additionally, other information serving protocols may be employed across various ports, e.g., FTP communications across port, and/or the like. An information server may communicate to and/or with other components in a component collection, including itself, and/or facilities of the like. Most frequently, the information server communicates with the database, operating systems, other program components, user interfaces, Web browsers, and/or the like.

Access to the database may be achieved through a number of database bridge mechanisms such as through scripting languages as enumerated below (e.g., CGI) and through inter-application communication channels as enumerated below (e.g., CORBA, WebObjects, etc.). Any data requests through a Web browser are parsed through the bridge mechanism into appropriate grammars as required by disclosed embodiments. In one embodiment, the information server would provide a Web form accessible by a Web browser. Entries made into supplied fields in the Web form are tagged as having been entered into the particular fields, and parsed as such. The entered terms are then passed along with the field tags, which act to instruct the parser to generate queries directed to appropriate tables and/or fields. In one embodiment, the parser may generate queries in standard SQL by instantiating a search string with the proper join/select commands based on the tagged text entries, wherein the resulting command is provided over the bridge mechanism to disclosed embodiments as a query. Upon generating query results from the query, the results are passed over the bridge mechanism, and may be parsed for formatting and generation of a new results Web page by the bridge mechanism. Such a new results Web page is then provided to the information server, which may supply it to the requesting Web browser.

Also, an information server may contain, communicate, generate, obtain, and/or provide program component, system, user, and/or data communications, requests, and/or responses.

User Interface

Computer interfaces in some respects are similar to automobile operation interfaces. Automobile operation interface elements such as steering wheels, gearshifts, and speedometers facilitate the access, operation, and display of automobile resources, and status. Computer interaction interface elements such as check boxes, cursors, menus, scrollers, and windows (collectively and commonly referred to as widgets) similarly facilitate the access, capabilities, operation, and display of data and computer hardware and operating system resources, and status. Operation interfaces are commonly called user interfaces. Graphical user interfaces (GUIs) such as the Apple Macintosh Operating System's Aqua, IBM's OS/2, Microsoft's Windows 2000/2003/3.1/95/98/CE/Millennium/NT/XPNi sta/7 (i.e., Aero), Unix's X-Windows (e.g., which may include additional Unix graphic interface libraries and layers such as K Desktop Environment (KDE), mythTV and GNU Network Object Model Environment (GNOME)), web interface libraries (e.g., ActiveX, AJAX, (D)HTML, FLASH, Java, JavaScript, etc. interface libraries such as, but not limited to, Dojo, jQuery(UI), MooTools, Prototype, script.aculo.us, SWFObject, Yahoo! User Interface, any of which may be used and) provide a baseline and means of accessing and displaying information graphically to users.

A user interface component is a stored program component that is executed by a CPU. The user interface may be a conventional graphic user interface as provided by, with, and/or atop operating systems and/or operating environments such as already discussed. The user interface may allow for the display, execution, interaction, manipulation, and/or operation of program components and/or system facilities through textual and/or graphical facilities. The user interface provides a facility through which users may affect, interact, and/or operate a computer system. A user interface may communicate to and/or with other components in a component collection, including itself, and/or facilities of the like. Most frequently, the user interface communicates with operating systems, other program components, and/or the like. The user interface may contain, communicate, generate, obtain, and/or provide program component, system, user, and/or data communications, requests, and/or responses.

Web Browser

A Web browser component is a stored program component that is executed by a CPU. The Web browser may be a conventional hypertext viewing application such as Microsoft Internet Explorer or Netscape Navigator. Secure Web browsing may be supplied with 128 bit (or greater) encryption by way of HTTPS, SSL, and/or the like. Web browsers allowing for the execution of program components through facilities such as ActiveX, AJAX, (D)HTML, FLASH, Java, JavaScript, web browser plug-in APIs (e.g., FireFox, Safari Plug-in, and/or the like APIs), and/or the like. Web browsers and like information access tools may be integrated into PDAs, cellular telephones, and/or other mobile devices. A Web browser may communicate to and/or with other components in a component collection, including itself, and/or facilities of the like. Most frequently, the Web browser communicates with information servers, operating systems, integrated program components (e.g., plug-ins), and/or the like; e.g., it may contain, communicate, generate, obtain, and/or provide program component, system, user, and/or data communications, requests, and/or responses. Of course, in place of a Web browser and information server, a combined application may be developed to perform similar functions of both. The combined application would similarly affect the obtaining and the provision of information to users, user agents, and/or the like from the enabled nodes. The combined application may be nugatory on systems employing standard Web browsers.

Mail Server

A mail server component is a stored program component that is executed by a CPU. The mail server may be a conventional Internet mail server such as, but not limited to sendmail, Microsoft Exchange, and/or the like. The mail server may allow for the execution of program components through facilities such as ASP, ActiveX, (ANSI) (Objective-) C (++), C# and/or .NET, CGI scripts, Java, JavaScript, PERL, PHP, pipes, Python, WebObjects, and/or the like. The mail server may support communications protocols such as, but not limited to: Internet message access protocol (IMAP), Messaging Application Programming Interface (MAPI)/Microsoft Exchange, post office protocol (POP3), simple mail transfer protocol (SMTP), and/or the like. The mail server can route, forward, and process incoming and outgoing mail messages that have been sent, relayed and/or otherwise traversing through and/or to the present invnetion.

Access to the mail may be achieved through a number of APIs offered by the individual Web server components and/or the operating system.

Also, a mail server may contain, communicate, generate, obtain, and/or provide program component, system, user, and/or data communications, requests, information, and/or responses.

Mail Client

A mail client component is a stored program component that is executed by a CPU. The mail client may be a conventional mail viewing application such as Apple Mail, Microsoft Entourage, Microsoft Outlook, Microsoft Outlook Express, Mozilla, Thunderbird, and/or the like. Mail clients may support a number of transfer protocols, such as: IMAP, Microsoft Exchange, POP3, SMTP, and/or the like. A mail client may communicate to and/or with other components in a component collection, including itself, and/or facilities of the like. Most frequently, the mail client communicates with mail servers, operating systems, other mail clients, and/or the like; e.g., it may contain, communicate, generate, obtain, and/or provide program component, system, user, and/or data communications, requests, information, and/or responses. Generally, the mail client provides a facility to compose and transmit electronic mail messages.

Cryptographic Server

A cryptographic server component is a stored program component that is executed by a CPU, cryptographic processor, cryptographic processor interface, cryptographic processor device, and/or the like. Cryptographic processor interfaces will allow for expedition of encryption and/or decryption requests by the cryptographic component, however, the cryptographic component, alternatively, may run on a conventional CPU. The cryptographic component allows for the encryption and/or decryption of provided data. The cryptographic component allows for both symmetric and asymmetric (e.g., Pretty Good Protection (PGP)) encryption and/or decryption. The cryptographic component may employ cryptographic techniques such as, but not limited to: digital certificates (e.g., X.509 authentication framework), digital signatures, dual signatures, enveloping, password access protection, public key management, and/or the like. The cryptographic component will facilitate numerous (encryption and/or decryption) security protocols such as, but not limited to: checksum, Data Encryption Standard (DES), Elliptical Curve Encryption (ECC), International Data Encryption Algorithm (IDEA), Message Digest 5 (MD5, which is a one way hash function), passwords, Rivest Cipher (RC5), Rijndael, RSA (which is an Internet encryption and authentication system that uses an algorithm developed in 1977 by Ron Rivest, Adi Shamir, and Leonard Adleman), Secure Hash Algorithm (SHA), Secure Socket Layer (SSL), Secure Hypertext Transfer Protocol (HTTPS), and/or the like. Employing such encryption security protocols, disclosed embodiments may encrypt all incoming and/or outgoing communications and may serve as node within a virtual private network (VPN) with a wider communications network. The cryptographic component facilitates the process of "security authorization" whereby access to a resource is inhibited by a security protocol wherein the cryptographic component effects authorized access to the secured resource. In addition, the cryptographic component may provide unique identifiers of content, e.g., employing and MD5 hash to obtain a unique signature for an digital audio file. A cryptographic component may communicate to and/or with other components in a component collection, including itself, and/or facilities of the like. The cryptographic component supports encryption schemes allowing for the secure transmission of information across a communications network to enable the component to engage in secure transactions if so desired. The cryptographic component facilitates the secure accessing of resources on disclosed embodiments and facilitates the access of secured resources on remote systems; i.e., it may act as a client and/or server of secured resources. Most frequently, the cryptographic component communicates with information servers, operating systems, other program components, and/or the like. The cryptographic component may contain, communicate, generate, obtain, and/or provide program component, system, user, and/or data communications, requests, and/or responses.

The Database

The database component may be embodied in a database and its stored data. The database is a stored program component, which is executed by the CPU; the stored program component portion configuring the CPU to process the stored data. The database may be a conventional, fault tolerant, relational, scalable, secure database such as Oracle or Sybase. Relational databases are an extension of a flat file. Relational databases consist of a series of related tables. The tables are interconnected via a key field. Use of the key field allows the combination of the tables by indexing against the key field; i.e., the key fields act as dimensional pivot points for combining information from various tables. Relationships generally identify links maintained between tables by matching primary keys. Primary keys represent fields that uniquely identify the rows of a table in a relational database. More precisely, they uniquely identify rows of a table on the "one" side of a one-to-many relationship.

Alternatively, the database may be implemented using various standard data-structures, such as an array, hash, (linked) list, struct, structured text file (e.g., XMiL), table, and/or the like. Such data-structures may be stored in memory and/or in (structured) files. In another alternative, an object-oriented database may be used, such as Frontier, ObjectStore, Poet, Zope, and/or the like. Object databases can include a number of object collections that are grouped and/or linked together by common attributes; they may be related to other object collections by some common attributes. Object-oriented databases perform similarly to relational databases with the exception that objects are not just pieces of data but may have other types of functionality encapsulated within a given object. If the database is implemented as a data-structure, the use of the database may be integrated into another component such as the component. Also, the database may be implemented as a mix of data structures, objects, and relational structures. Databases may be consolidated and/or distributed in countless variations through standard data processing techniques. Portions of databases, e.g., tables, may be exported and/or imported and thus decentralized and/or integrated.

In one embodiment, the database component includes several tables. A Users (e.g., operators and physicians) table may include fields such as, but not limited to: user_id, ssn, dob, first_name, last_name, age, state, address_firstline, address_secondline, zipcode, devices_list, contactinfo, contact_type, alt_contact_info, alt_contact_type, and/or the like to refer to any type of enterable data or selections discussed herein. The Users table may support and/or track multiple entity accounts. A Clients table may include fields such as, but not limited to: user_id, client_id, client_ip, client_type, client_model, operating_system, os_version, app_installed_flag, and/or the like. An Apps table may include fields such as, but not limited to: app_ID, app_name, app_type, OS_compatibilities_list, version, timestamp, developer_ID, and/or the like. A beverages table including, for example, heat capacities and other useful parameters of different beverages, such as depending on size beverage_name, beverage_size, desired_coolingtemp, cooling_time, favorite_drinker, number_of_beverages, current_beverage_temperature, current_ambient_temperature, and/or the like. An Parameter table may include fields including the foregoing fields, or additional ones such as cool_start_time, cool_preset, cooling_rate, and/or the like. A Cool Routines table may include a plurality of cooling sequences may include fields such as, but not limited to: sequence_type, sequence_id, flow_rate, avg_water_temp, cooling_time, pump_setting, pump_speed, pump_pressure, power_level, temperature_sensorid_number, temperature_sensor_location, and/or the like.

In one embodiment, user programs may contain various user interface primitives, which may serve to update the platform. Also, various accounts may require custom database tables depending upon the environments and the types of clients the system may need to serve. It should be noted that any unique fields may be designated as a key field throughout. In an alternative embodiment, these tables have been decentralized into their own databases and their respective database controllers (i.e., individual database controllers for each of the above tables). Employing standard data processing techniques, one may further distribute the databases over several computer systemizations and/or storage devices. Similarly, configurations of the decentralized database controllers may be varied by consolidating and/or distributing the various database components. The system may be configured to keep track of various settings, inputs, and parameters via database controllers.

Data Communication

In currently preferred embodiments, data and messages may be transmitted and/or received using any appropriate wireless technology, such as CAT-M (Cat-M refers to Category M, the second generation of LTE chipsets meant for IoT applications. The "M" initially stood for "machines." Category M follows the Category-1 LTE, part of the existing 3GPP LTE standards, which enables reduced power consumption and cost by capping speeds at 10 megabits per second.); cellular technology compliant with at least one one of 2G, 3G, 4G, and 5G standards, and any cellular technology.

Device Expansion Platform

Embodiments of a system that includes apparatus 100 may include one or more devices configured to be communicatively coupled to the apparatus. Such devices may be communicatively coupled to the apparatus using any suitable short-range wired or wireless communication technology. For example, communication can be achieved by connecting a full-size or micro USB port on the device to a micro USB port on apparatus 100, either through a cable or by directly coupling a male connector on the device to a female connector on the apparatus 100. Such an arrangement may be preferred, for example, in a docking station with a male USB connector extending into a cradle configured to receive apparatus 100. Alternatively or in addition, a wireless communication connection between the docking station and apparatus 100 may be effected using any appropriate short-range wireless technology, such as so-called Bluetooth Low Energy (BLE or Bluetooth LE, and marketed as Bluetooth Smart); Near Field Communication (NFC), or other wireless (wi-fi or other RF) technology. Other devices may similarly use a short range wireless air interface to communicate with apparatus 100, such as a scale for measuring a user's weight, a blood pressure (BP) cuff, insulin pen, heart rate monitor, oxygen dispenser, or other self-administered medical device.

In embodiments, a FreeStyle Libre (FL)-like arrangement may be used for collecting blood glucose monitor readings. For example, glucose sensors may be inserted in the user's subcutaneous tissue, and the user may obtain a current glucose level by scanning with a suitably configured device communicatively coupled to, or included in, apparatus 100.

Biometric ID Capabilities

In embodiments, a biometric ID capability may be used to identify the user to apparatus 100, for example, in an environment such as a hospital in which a plurality of patients may be set up to use apparatus 100. In embodiments, apparatus 100 may be one of a plurality of apparatuses, any of which may be used by any of a plurality of patients. Such ID capabilities may be embodied, for example, in a fingerprint reader, a facial recognition scanner, an Eye Scanner, a Voice Recognition device, or the like.

On Meter Algorithms

In embodiments, updates to firmware and software applications installed in apparatus 100 may be provided using over the air (OTA) communications, or may be effected, for example, when apparatus 100 is physically coupled to a docking station.

In embodiments, apparatus 100 may execute any of a plurality of programs configured to perform any of a plurality of algorithms. For example, a program that identifies, displays, sends data, and/or sends messages pertaining to bG readings that exceed a predetermined high or low threshold. The program may additionally or alternatively determine, display, and/or generate alerts, trends, Time in Range, Insulin Dosing Calculations, and provide for two-way communication capabilities customized with personal information or the like.

Although certain exemplary embodiments have been described with a certain degree of particularity, it is to be understood that the present disclosure has been made only by way of illustration and that numerous changes in the details of construction and arrangement of parts may be implemented to without departing from the spirit and the scope of the invention.

What is claimed is:

1. An apparatus for obtaining and transmitting medical test data, the apparatus comprising:
    a housing containing a processor operably coupled to a memory and a power source, wherein the memory stores computer-executable instructions and the processor executes the instructions to cause the apparatus to perform functions;
    a display operatively coupled to the processor for displaying information associated with at least one medical test;
    a wireless transceiver configured to send data of the medical test to a remote location to be recorded in a central database, using at least one of an email service, a short message service (SMS), an instant messaging service (IM), an Unstructured Supplementary Service Data (USSD) service, a Greedy Perimeter Stateless Routing (GPSR) service, a Global System for Mobile communications (GSM) service, a fax service, a Category-M service, a 2G service, a 3G service, a 4G service, and a 5G service;
    an A1c detector operably coupled to the processor that is at least one of an A1c meter and an A1c estimator that estimates A1c based on a plurality of blood glucose (bG) readings obtained from a glucometer contained in the housing;
    wherein the medical test is the detection of an A1c value by the A1c detector.

2. The apparatus of claim 1, wherein the A1c detector is an A1c meter that determines an A1c level using a blood sample.

3. The apparatus of claim 1, wherein the A1c detector estimates an A1c level based on a plurality of blood glucose (bG) measurements each taken using a respective blood sample.

4. The apparatus of claim 1, wherein:
    the wireless transceiver is configured to send the medical test data using at least three different wireless services; and a first one of the wireless services sends the medical test data to the remote location, and in the event a confirmation of receipt of the medical test data sent using the first service is not received, a second service sends the medical test data to the remote location, and in the event a confirmation of receipt of the medical test data sent using the second service is not received, a third service sends the medical test data to the remote location, and in the event a confirmation of receipt of the medical test data sent using the third service is not received, the medical test data is stored in the memory for resending the next time a reading is taken.

5. The apparatus of claim 1 further comprising a docking station removably coupled to the external housing.

6. The apparatus of claim 5 wherein the docking station comprises a charging device configured to charge the power source when the external housing is physically coupled to the docking station.

7. The apparatus of claim 1 further comprising a radio frequency identification (RFID) dongle removably coupled to the housing for identifying the apparatus to an external device.

8. The apparatus of claim 1, wherein the apparatus is configured to communicate wirelessly to at least one external device that is an external weight scale, a blood pressure (BP) cuff, an insulin pen, a heart rate monitor, or an oxygen dispenser.

9. The apparatus of claim 8, wherein the apparatus is configured to wirelessly communicate with the at least one external device using at least one short range wireless technology that includes at least one of Bluetooth Low Energy (BLE), Near Field Communication (NFC), or Wi-Fi.

10. The apparatus of claim 1, further comprising a user identifying device that determines the user's ID using biometric data obtained from the user by the device.

11. The apparatus of claim 10, wherein the biometric data includes at least one of a fingerprint, an eye scan, an image of the user's face, and a sample of the user's voice.

12. The apparatus of claim 1, wherein the functions performed by the apparatus include at least one of determining whether a predetermined high or low medical test threshold has been exceeded.

13. The apparatus of claim 12, wherein the medical test is one of a blood glucose test and an A1c determination.

14. The apparatus of claim 1, wherein the functions performed by the apparatus include at least one of generating an alert, determining a trend, determining a Time in Range, and Calculating an Insulin Dose.

15. The apparatus of claim 1, wherein the functions performed by the apparatus include generating and sending a message that includes personal information obtained from storage and information based on at least one medical test result.

* * * * *